(12) United States Patent
Kiani et al.

(10) Patent No.: US 7,844,313 B2
(45) Date of Patent: Nov. 30, 2010

(54) PULSE OXIMETRY SENSOR ADAPTER

(75) Inventors: Massi E. Kiani, Laguna Niguel, CA (US); Robert A. Smith, Lake Forest, CA (US); David R. Tobler, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 1313 days.

(21) Appl. No.: 11/341,999

(22) Filed: Jan. 27, 2006

(65) Prior Publication Data

US 2006/0189859 A1     Aug. 24, 2006

Related U.S. Application Data

(60) Continuation of application No. 10/624,446, filed on Jul. 22, 2003, now Pat. No. 6,993,371, which is a continuation of application No. 09/982,453, filed on Oct. 17, 2001, now Pat. No. 6,597,933, which is a division of application No. 09/404,060, filed on Sep. 23, 1999, now Pat. No. 6,349,228, which is a continuation of application No. 09/021,957, filed on Feb. 11, 1998, now Pat. No. 5,995,855.

(51) Int. Cl.
*A61B 5/00* (2006.01)
*A61B 5/1455* (2006.01)

(52) U.S. Cl. .................. 600/310; 600/322; 600/323

(58) Field of Classification Search ............... 600/310, 600/322, 323, 344
See application file for complete search history.

(56) References Cited

U.S. PATENT DOCUMENTS

| | | | |
|---|---|---|---|
| 4,684,245 A | 8/1987 | Goldring | |
| 5,249,576 A | 10/1993 | Goldberger et al. | |
| 5,287,853 A | 2/1994 | Vester et al. | |
| 5,387,122 A | 2/1995 | Goldberger et al. | |
| 5,632,272 A | 5/1997 | Diab et al. | |
| 5,758,644 A | 6/1998 | Diab et al. | |
| 5,769,785 A | 6/1998 | Diab et al. | |
| 5,782,757 A | 7/1998 | Diab et al. | |
| 5,807,247 A | 9/1998 | Merchant et al. | |
| 5,818,985 A | 10/1998 | Merchant et al. | |
| 5,830,137 A | 11/1998 | Scharf | |
| 5,995,855 A | 11/1999 | Kiani et al. | |

(Continued)

FOREIGN PATENT DOCUMENTS

EP     0 538 631 A1     9/1992

*Primary Examiner*—Eric F Winakur
(74) *Attorney, Agent, or Firm*—Knobbe, Martens, Olson & Bear LLP

(57) ABSTRACT

An adapter allows the interconnection of a sensor originating from one manufacturer to be coupled with conventionally incompatible monitors originating from other manufacturers to form a properly functioning pulse oximetry system. The adapter matches a sensor driver in a monitor to the current requirements and light source configuration of a sensor. The adapter also matches a sensor's light detector signal level to the dynamic range requirements of a monitor preamplifier. Further, the adapter provides compatible sensor calibration, sensor type and security information to a monitor. The adapter may have a self-contained power source or it may derive power from the monitor, allowing both passive and active adapter components. The adapter is particular suited as an adapter cable, replacing a conventional patient cable or sensor cable as the interconnection between a sensor to a monitor in a pulse oximetry system.

15 Claims, 18 Drawing Sheets

U.S. PATENT DOCUMENTS

| | | |
|---|---|---|
| 5,995,858 A | 11/1999 | Kinast |
| 6,002,952 A | 12/1999 | Diab et al. |
| 6,061,584 A | 5/2000 | Lovejoy et al. |
| 6,349,228 B1 | 2/2002 | Kiani et al. |
| 6,597,933 B2 | 7/2003 | Kiani et al. |
| 6,697,656 B1 | 2/2004 | Al-Ali |

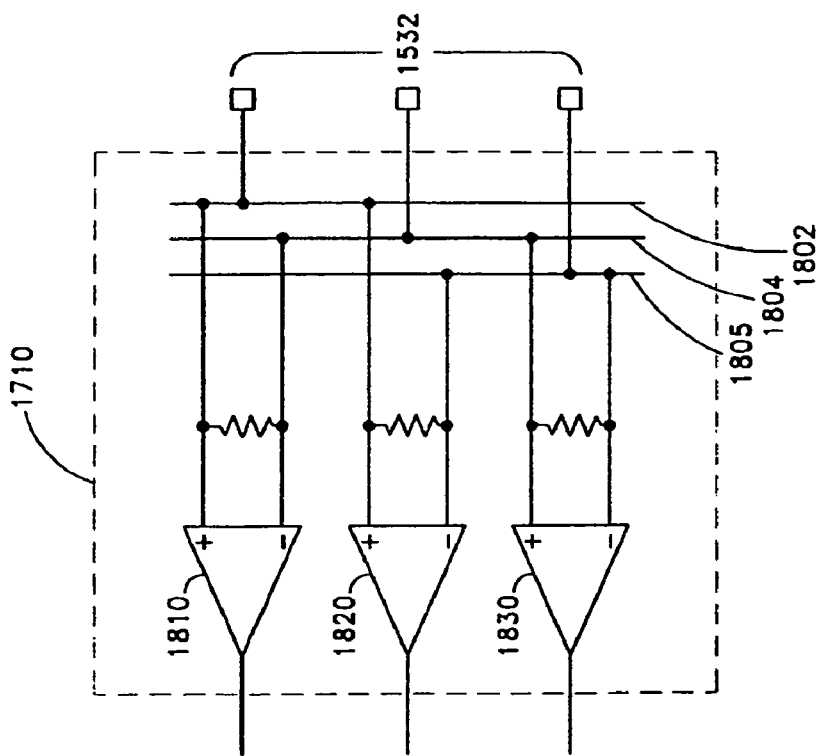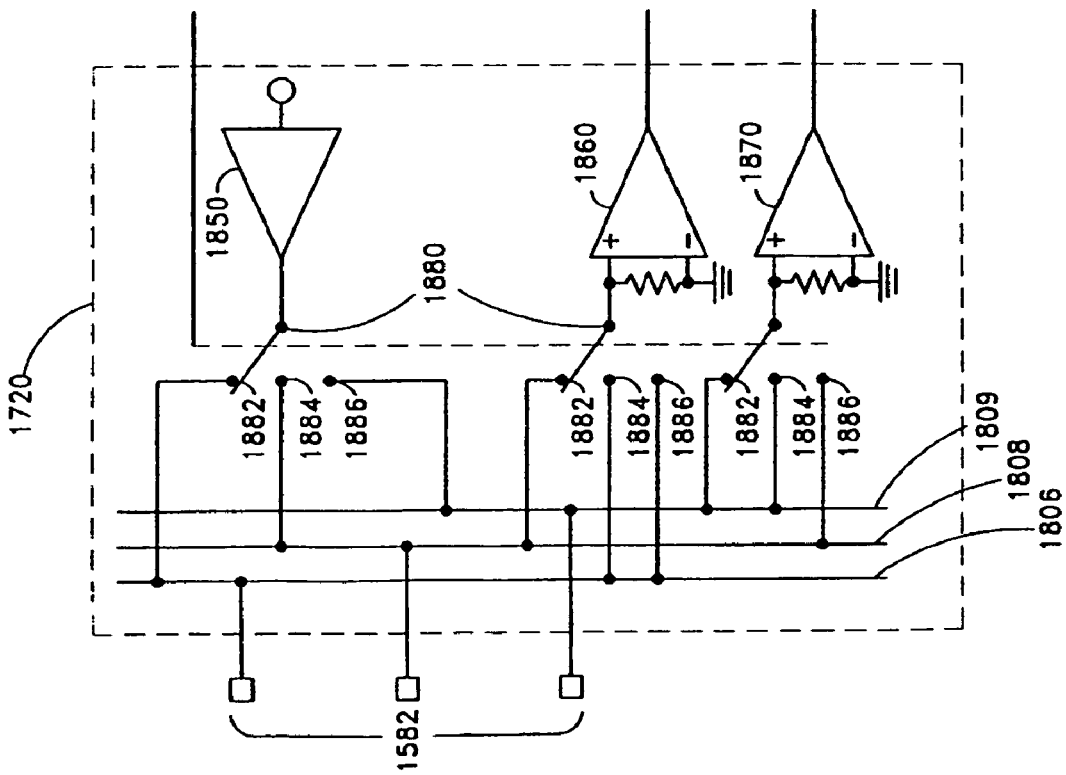
FIG. 18

PULSE OXIMETRY SENSOR ADAPTER

RELATED APPLICATION

This is a continuation application based on application Ser. No. 10/624,446, filed Jul. 22, 2003 now U.S. Pat. No. 6,993,371, which is a continuation of application Ser. No. 09/982,453, filed Oct. 17, 2001, now U.S. Pat. No. 6,597,933, which is a divisional of application Ser. No. 09/404,060, filed Sep. 23, 1999, now U.S. Pat. No. 6,349,228, which is a continuation of application Ser. No. 09/021,957, filed on Feb. 11, 1998, now U.S. Pat. No. 5,995,855, the entirety of which is incorporated herein by reference.

BACKGROUND OF THE INVENTION

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximetry system consists of a sensor attached to a patient, a monitor, and a cable connecting the sensor and monitor.

Conventionally, a pulse oximetry sensor has both red and infrared LED emitters and a photodiode detector. The sensor is typically attached to an adult patient's finger or an infant patient's foot. For a finger, the sensor is configured so that the emitters project light through the fingernail and into the blood vessels and capillaries underneath. The photodiode is positioned at the finger tip opposite the fingernail so as to detect the LED emitted light as it emerges from the finger tissues.

The pulse oximetry monitor determines oxygen saturation by computing the differential absorption by arterial blood of the two wavelengths emitted by the sensor. The monitor alternately activates the sensor LED emitters and reads the resulting current generated by the photodiode detector. This current is proportional to the intensity of the detected light. A ratio of detected red and infrared intensities is calculated by the monitor, and an arterial oxygen saturation value is empirically determined based on the ratio obtained. The monitor contains circuitry for controlling the sensor, processing sensor signals and displaying a patient's oxygen saturation, heart rate and plethysmographic waveform. A pulse oximetry monitor is described in U.S. Pat. No. 5,632,272 assigned to the assignee of the present invention.

The patient cable provides conductors between a first connector at one end, which mates to the sensor, and a second connector at the other end which mates to the monitor. The conductors relay the drive currents from the monitor to the sensor emitters and the photodiode detector signals from the sensor to the monitor.

SUMMARY OF THE INVENTION

A drawback to conventional pulse oximetry systems is the lack of standardization of the sensor and the monitor. Unless the sensor and the monitor are manufactured by the same company, it is unlikely that these two components can be connected as a functioning pulse oximetry system. This incompatibility is mainly due to physical configuration and signal parameter differences among both the sensors and the monitors. Sensors differ primarily with respect to the configuration, drive requirements and wavelength of the LEDs. Sensors also differ in the configuration and value of coding and calibration resistors used to identify, for example, sensor type or LED wavelength. Monitors differ primarily with respect to the configuration and current limit of the LED driver; the amount of preamplifier gain applied to the photodiode detector signal; and the method of reading and interpreting sensor coding and calibration resistors. Further, the physical interface between sensors and monitors, such as connector types and pinouts, is also variable. Sensor and monitor variations among various pulse oximetry systems are discussed in detail below with respect to FIGS. 1 through 3.

FIG. 1 depicts one type of sensor 100 and a corresponding monitor 150 for one type of pulse oximetry system. For this particular sensor 100, the red LED 110 and infrared LED 120 are connected back-to-back and in parallel. That is, the anode 112 of the red LED 110 is connected to the cathode 124 of the infrared LED 120 and the anode 122 of the infrared LED 120 is connected to the cathode 114 of the red LED 110. Also for this sensor 100, the photodiode detector 130 is configured so that the photodiode leads 102, 104 are not in common with either of the LED leads 106, 108.

As shown in FIG. 1, the sensor 100 is also configured with a coding resistor 140 in parallel with the LEDs 110, 120. The coding resistor 140 is provided as an indicator that can be read by the monitor 150, as described in pending U.S. patent application Ser. No. 08/478,493, filed Jun. 7, 1995 and assigned to the assignee of the present application. The resistor 140 is used, for example, to indicate the type of sensor 100. In other words, the value of the coding resistor 140 can be selected to indicate that the sensor 100 is an adult probe, a pediatric probe, a neonatal probe, a disposable probe or a reusable probe. The coding resistor 140 is also utilized for security purposes. In other words, the value of the coding resistor 140 is used to indicate that the sensor 100 is from an authorized sensor supplier. This permits control over safety and performance concerns which arise with unauthorized sensors. In addition, the coding resistor 140 is used to indicate physical characteristics of the sensor 100, such as the wavelengths of the LEDs 110, 120.

Also shown in FIG. 1 is a portion of a monitor 150 that is compatible with the sensor described above. The monitor 150 has drive circuitry that includes a pair of current drivers 162, 164 and a switching circuit 170. The monitor 150 also has a signal conditioner, which includes an input buffer 195 that conditions the output of the sensor photodiode 130. In addition, the monitor has a low-voltage source 164 and corresponding reference resistor 194 that read the sensor coding resistor 140.

Each current driver 162, 164 provides one of the LEDs 110, 120 with a predetermined activation current as controlled by the switching circuit 170. The switching circuit 170, functionally, is a double-pole, triple throw (2P3T) switch. A first switch 172 connects to a first LED lead 106 and a second switch 174 connects to a second LED lead 108. The first switch 172 has a first position 181 connected to the red LED driver 162; a second position 182 connected to a reference resistor 194 and a buffer 195; and a third position 183 connected to ground 168. The second switch 174 has a first position 181 connected to ground 168; a second position 182 connected to a low-voltage source 192; and a third position 183 connected to the infrared LED driver 164.

During a particular time interval, the switching circuit 170 causes the first switch 172 to connect the red LED driver 162 to the red LED anode 112 and simultaneously causes the second switch 174 to connect the ground 168 to the red LED cathode 114. As a result, a forward current is established in the red LED 110, which is activated to emit light. During another particular time interval, the switching circuit 170 causes the first switch 172 to connect the ground 168 to the infrared LED cathode 124 and simultaneously causes the second switch 174 to connect the infrared LED driver 164 to the infrared LED anode 122. As a result, a forward current is established in the infrared LED, which is activated to emit light. This cycle is repeated to cause the sensor to alternately emit red and infrared light. These alternating light pulses result in currents in the photodiode detector 130, which are input to a monitor buffer 166 and multiplexed 197 into an analog-to-digital converter (ADC) 199. The digitized outputs from the ADC 199, representing detected intensities, are then processed by the monitor 150 and displayed as oxygen status.

During a monitor initialization interval, the switching circuit 170 causes the first and second switches 172, 174 to be in a second position 182. This isolates the LED leads 106, 108 from the drivers 162, 164 and ground 168. Further, the low-voltage source 192 is connected to one LED lead 108 and the reference resistor 194 is connected to the other LED lead 106. As a result, a voltage is established across the parallel combination of the coding resistor 140 and the LEDs 110, 120. If this voltage is less than the forward voltage of the forward biased infrared LED 120, then, because the red LED 110 is reverse biased, neither LED 110, 120 conducts significant current. In such a scenario, the current that passes through the parallel combination of the red LED 110, infrared LED 120, and coding resistor 140 is approximately equal to the current through the coding resistor 140. Thus, the equivalent circuit is the low-voltage source 192 across the series combination of the coding resistor 140 and the reference resistor 194. The resistance of the coding resistor 140 is then easily determined via Ohms Law from the voltage across the reference resistor 194, which is read as a digitized value from the ADC 199.

FIG. 2 depicts another type of sensor 200 and corresponding monitor 250 for a conventional pulse oximetry system. This pulse oximetry system is described in U.S. Pat. No. 4,621,643 to New Jr. et al., issued Nov. 11, 1986. The sensor 200 of FIG. 2 is similar to that of FIG. 1 in that it comprises a red LED 210 and an infrared LED 220. However, in this sensor 200, the LEDs 210, 220 are in a common cathode, three-wire configuration. That is, the cathode 214 of the red LED 210 is connected to the cathode 224 of the infrared LED 220 and a common input lead 208. Also, the anode 212 of the red LED 210 and the anode 222 of the infrared LED 220 have separate input leads 202, 204. The photodiode detector 230 shown in FIG. 2 functions in much the same way as the detector 130 shown in FIG. 1 but shares one input lead 208 with the sensor LEDs 210, 220. As shown in FIG. 2, the sensor 200 also has a calibration resistor 240 with one separate input lead 206 and one lead 208 in common with the LEDs 210, 220 and photodiode 230. This resistor 240 is encoded to correspond to the measured wavelength combination of the red LED 210 and infrared LED 220.

Also shown in FIG. 2 is a portion of a monitor 250 that is compatible with the depicted sensor 200. The monitor 250 has LED drive circuitry 260 which activates the LEDs 210, 220 one at time with a predetermined drive current independently applied to each of the LED anodes 212, 222. The monitor 250 also has a signal conditioner, including amplification and filtration circuitry 270 that conditions the input current from the detector 230, which is multiplexed 282 into a successive-approximation analog-to-digital converter (ADC) 284 comprising a comparator 285 and digital-to-analog converter (DAC) 286. A microprocessor 288 then reads the digitized detector signal for analysis. The monitor 250 reads the calibration resistor 240 by passing a predetermined current from a current source 290 through the resistor 240. The microprocessor 288 reads the resulting voltage across the resistor 240, which is passed through the multiplexer 282 and ADC 284. The microprocessor 288 then computes the resistor value per Ohm's Law.

FIG. 3 illustrates yet another type of sensor 300 and corresponding monitor 350. This configuration is similar to those of FIGS. 1 and 2 in that the sensor 300 has a red LED 310, an infrared LED 320 and a photodiode detector 330. The configuration of the LEDs 310, 320 and the corresponding LED driver 360, however, differ from those previously described. The LED driver 360 has a voltage source 362, a red LED current sink 364 and an infrared LED current sink 367. The LEDs 310, 320 are arranged in a three-wire, common-anode configuration. That is, the red LED anode 312 and the infrared LED anode 322 have a common anode lead 302, the red LED cathode 314 has one separate lead 304 and the infrared LED cathode 324 has another separate lead 305. The voltage source output 352 connects to the common anode lead 302, the red LED current sink input 354 connects to the red LED cathode lead 304, and the infrared LED current sink input 355 connects to the infrared LED cathode lead 305.

The current sinks 364, 367 control the drive current through each LED 310, 320. The voltage source 362 has sufficient output capability to supply this drive current to each LED 310, 320 individually. Each current sink 364, 367 is a grounded emitter transistor 365, 368 having a bias resistor 366, 369 and a base control input 372, 374 that switches each transistor 365, 368 on and off. The bias resistor value and voltage of the base control input determine the amount of LED drive current. In operation, the red and infrared LEDs 310, 320 are alternately activated by pulsed control signals alternately applied to the base control inputs 372, 374.

The detector portion of the sensor 300 of FIG. 3 also differs from those in the previously miniature described sensors in that a gain resistor 340 is connected to the photodiode 330. When connected to the corresponding monitor 350, the gain resistor 340 provides feedback, which adjusts the gain of a monitor preamplifier within the signal conditioner portion 380 of the monitor 350, which reduces the preamplifier dynamic range requirements. For example, if the sensor 300 is configured for neo-natal patients, where the sensor site is of relatively narrow thickness and the skin relatively transparent, the gain can be correspondingly low. However, if the sensor 300 is configured for adult patients, with a relatively thick and opaque sensor site, such as a finger, the gain can be correspondingly higher to compensate for lower detected intensities.

FIGS. 1 through 3 are examples of just some of the functional variations between sensors and monitors in pulse oximetry systems. These functional variations thwart the use of different sensors on different monitors. There are other sensor and monitor variations not described above. For example, a sensor may have LEDs with a three-wire common-anode configuration, as depicted in FIG. 7 below. There are also other potential mismatches between sensors and monitors. For example, the LED drive current supplied by a particular monitor may be either too high or too low for the LEDs on an incompatible sensor.

Besides the functional variations described above, physical variations between sensors and monitors may prevent interconnection to form a pulse oximetry system. For example, sensors have a variety of connectors. These connectors may vary from subminiature D-type connectors to flex-circuit edge connectors to name a few. Similar connector variations exist on the monitor. Further, some pulse oximetry systems require a separate patient cable, which mates to the sensor at one end and the monitor at the other end to span the distance between patient and monitor. In other systems, the sensor incorporates a cable that plugs directly into a monitor. Another physical variation is the pinouts at both the sensor connector and monitor connector. That is, there are potential differences between what signals are assigned to what connector pins.

A conventional adapter cable can sometimes be used to interconnect two dissimilar devices. The connector at one end of the adapter cable is configured to mate with one device and the connector at the other end of the cable is configured to mate with the second device. The cable wires can be cross-connected as necessary to account for pinout differences. A conventional adapter cable, however, is of little use in interconnecting various sensors to various pulse oximetry monitors. As described above, although the sensors have similar components that perform similar functions, the incompatibilities are more than connector and pinout related. In particular, a conventional adapter cable is incapable of correcting for the signal mismatches between sensors and monitors.

Although it is perhaps possible to design sensors that accommodate a variety of monitors, such sensors would be, for the most part, commercially impractical. For one, pulse oximetry sensors can be either reusable or disposable. In the case of disposable sensors, cost per sensor is critical. Even for reusable sensors, cost and complexity are important design factors. A universal sensor having integrated adapter components could be significantly more expensive than the sensors described in FIGS. 1 through 3. A sensor adapter according to the present invention solves many of the problems associated with both sensor and monitor compatibility and the need to avoid sensor complexity.

One aspect of the present invention is an adapter that provides an interconnection between a pulse oximetry sensor and a monitor. The sensor has a light source and a light detector, and the monitor has a driver and a signal conditioner. The adapter comprises a plurality of signal paths. The signal paths are detachably connected to either the monitor, the sensor or both. A first signal path is in communication with the driver and the light source. A second signal path is in communication with the light detector and the signal conditioner. The adapter also comprises an adapter element that is connected to at least one of the signal paths. The adapter element modifies a characteristic of at least one of the signal paths so that the sensor and the monitor are jointly operable to measure oxygen status. In one embodiment, where the monitor has an information element detector in communication with at least one of the signal paths, the adapter element conveys information about the sensor that is compatible with the information element detector. In another embodiment, the adapter element is connected to the first signal path and matches the light source configuration with the driver configuration. In yet another embodiment, the adapter element is connected to the first signal path and matches the drive requirements of the light source with the drive capabilities of the driver. In an additional embodiment, the adapter element is connected to the second signal path and provides gain for a detector signal.

Another aspect of the present invention is a sensor adapter comprising a sensor having a light source and a light detector and comprising a plurality of signal paths. The signal paths are detachably connected to a monitor. A first signal path communicates a drive signal from the monitor to the light source. A second signal path communicates an intensity signal from the light detector to the monitor. The sensor adapter also comprises an adapter element in communication with at least one of the signal paths. The adapter element creates a compatibility signal that allows the sensor and the monitor to be jointly operable as a pulse oximetry system. In one embodiment, the sensor adapter comprises an active component. The active component generates a predetermined signal level applied to the first signal path that conveys information regarding a compatible sensor. In another embodiment of the sensor adapter, the light source has a conductive portion with a predetermined equivalent resistance that conveys information regarding a compatible sensor. Advantageously, the conductive portion may be an LED encapsulant or incorporated within the semiconductor material of an LED. In yet another embodiment, the sensor adapter further comprises a translator that senses a sensor information element and communicates equivalent information to the monitor.

Yet another aspect of the present invention is a method of connecting an incompatible sensor to a monitor. The method comprises the step of adapting a signal in communication with either the sensor, the monitor or both so that the sensor and the monitor are jointly operable as a pulse oximetry system. In one embodiment, the adapting step comprises the steps of sensing a drive signal and switching the drive signal to a particular one of a plurality of light source leads in response to the drive signal. Advantageously, the switching step may connect a two-wire driver to a three-wire light source or may connect a three-wire driver to a two-wire light source, either connection being made through a multiple-pole, multiple-throw switch. In another embodiment, the adapting step comprises adjusting a drive signal from the monitor to match the drive requirements of a light source in the sensor. In yet another embodiment, the adapting step comprises providing a feedback signal to the monitor. The amount of the feedback determines the gain applied within the monitor to a light detector signal from the sensor. In an additional embodiment, the adapting step comprises generating an information signal to an information element detector that corresponds to information from a compatible sensor. In another embodiment, the adapting step comprises translating an information signal from a sensor into a translated information signal that is read by an information element detector and corresponds to a compatible sensor.

A further aspect of the present invention is a sensor adapter for operably interconnecting an incompatible sensor to a monitor in a pulse oximetry system comprising an interconnect means for providing a signal path between the sensor and the monitor. The sensor adapter also comprises an adapter means for creating a compatible signal on the signal path. In one embodiment, the adapter means comprises a configuration means for routing a drive signal from the monitor so as to correspond to a light source in the sensor. In another embodiment, the adapter means comprises a limit means for changing the amount of a drive signal from the monitor so as to correspond to a light source in the sensor. In yet another embodiment, the adapter means comprises a gain means for modifying the amplitude of a detector signal from the sensor. In an additional embodiment, the adapter means comprises an information means for providing a signal to an information element detector that corresponds to a compatible sensor.

BRIEF DESCRIPTION OF THE DRAWINGS

The present invention is described in detail below in connection with the following drawing figures in which:

FIG. 18 is a schematic diagram of the driver test and sensor test portions of the configuration adapter.

DETAILED DESCRIPTION OF THE PREFERRED EMBODIMENT

Figure 4:
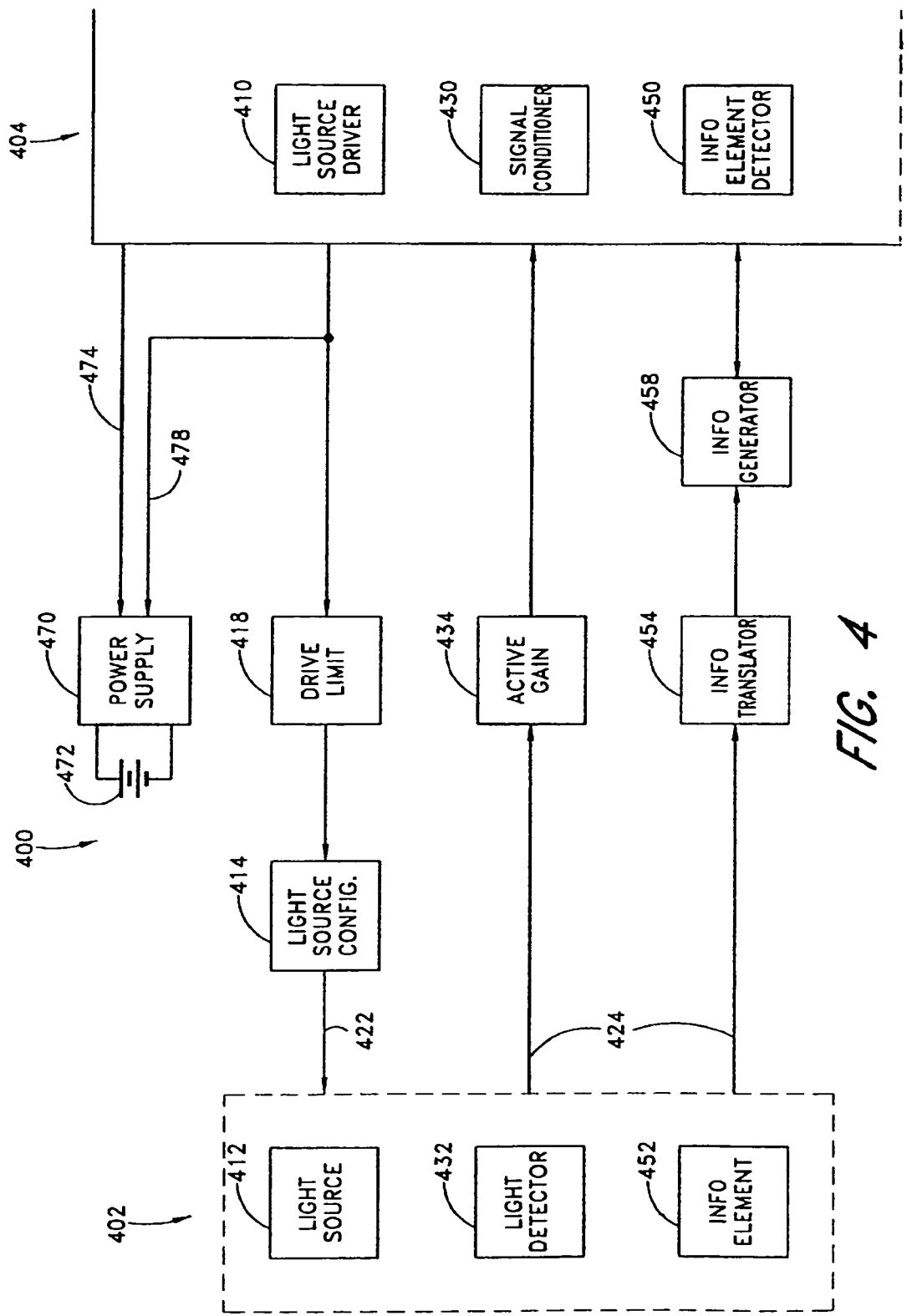
FIG. 4 is a block diagram of a sensor adapter according to the present invention.

FIG. 4 shows a functional block diagram of a sensor adapter 400 for interconnecting a sensor 402 to an incompatible monitor 404 in a pulse oximetry system. Interconnecting the monitor light source driver 410 with the sensor light source 412 are a light source configuration 414 adapter and a drive limit 418 adapter. The light source configuration 414 element adapts the light source driver 410 to the particular configuration of the sensor light source 412, such as two-wire, back-to-back LEDs, three-wire, common-anode LEDs and three-wire, common-cathode LEDs. The drive limit 418 element increases or decreases the current of the light source driver 410 to adapt to the requirements of the sensor light source 412.

Also shown in FIG. 4 is an active gain 434 element, which adapts the sensor light detector 432 to the monitor signal conditioner 430. Active gain 434 sets the amount of amplification of the signal from the sensor light detector 432 that occurs in the monitor signal conditioner 430. Active gain 434 may also provide preamplification of the light detector signal before input to the monitor 404.

FIG. 4 further shows a monitor information element detector 450 that is interconnected with an information generator 458 and information translator 454. The information generator 458 simulates an information element 452 on the sensor to provide the monitor information element detector 450 with information regarding, for example, sensor type, origin or light source calibration. The information translator 454 reads a sensor information element 452 and provides the equivalent information to the monitor information element detector 450, adapting to the configuration and value expected by the monitor 404.

As shown in FIG. 4, the sensor adapter 400 has a power supply 470. As such, the functions of the sensor adapter 400 as described above can be performed with both active and passive components. In one embodiment, the power supply 470 has an internal power source 472, such as a lithium-ion battery. In another embodiment, the power supply 470 uses an external power source. The external power source may be, for example, one or more d.c. voltages available from a monitor output 474. Alternatively, the external power source may be derived from the light source driver 410, which supplies pulsed power to the sensor light source 412. A fraction of this pulsed power can be routed by a tap 478 to the power supply 470, where it is a.c.-to-d.c. converted. Regardless of the power source, the power supply 470 may also include d.c.-to-d.c. conversion, filtering and voltage regulation to provide suitable voltage levels and power conditioning for the active components of the sensor adapter 400, as is well-known in the art.

Figure 5:
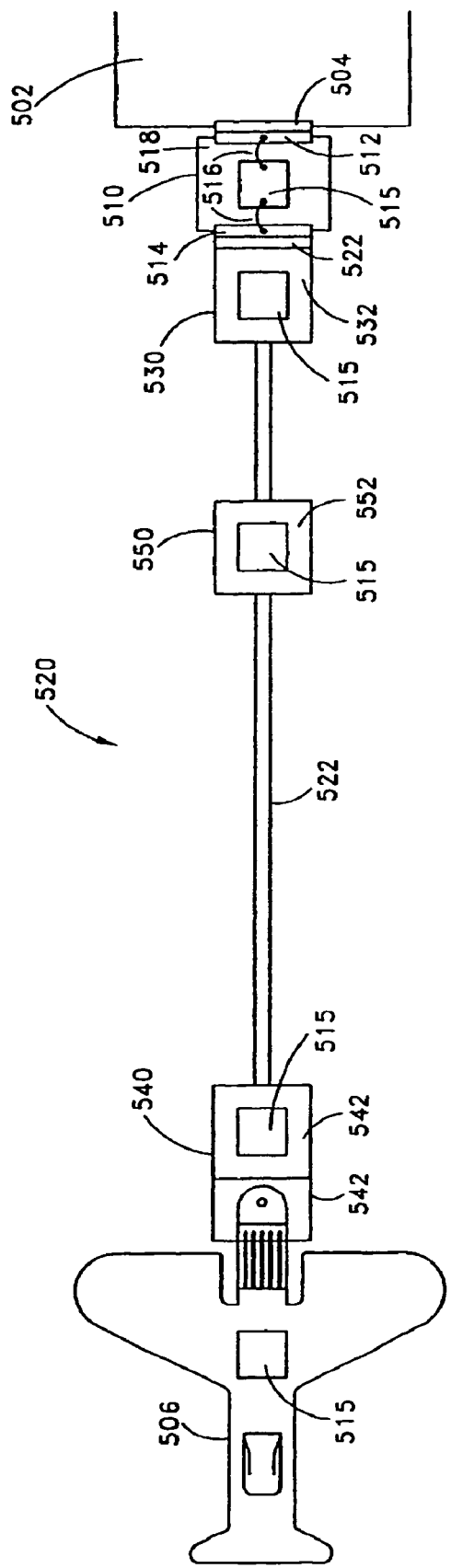
FIG. 5 is an illustration of various physical embodiments of a sensor adapter in relation to a sensor and a monitor.

FIG. 5 illustrates embodiments of the pulse oximetry sensor adapter according to the present invention. In one embodiment, the sensor adapter is configured as a connector block 510 that has a first connector 512 on one end that is attachable directly to a monitor 502 by plugging into a monitor connector 504 and a second connector 514 on the other end that accepts a cable connector 522. The components of the sensor adapter are mounted to a small substrate 515, and may be, for example, surface-mount devices soldered on one or both sides of a circuit board or flex-circuit. The substrate 515 is electrically interconnected to the connectors 512, 514. This interconnection may be done with conductors 516, such as individual wires, flex-circuit traces or ribbon cable soldered to both the substrate 515 and the connectors 512, 514. Alternatively, the substrate 515, might be directly attached to both connectors 512, 514. The substrate 515, conductors 516 and portions of the connectors 512, 514 are encapsulated by insulating material that forms the connector block body 518. One will recognize other possibilities for mounting and interconnecting the adapter components within the connector block 510.

FIG. 5 illustrates another embodiment of the sensor adapter where the adapter is configured as an adapter cable 520 that also serves the function and substitutes for a conventional patient cable or sensor cable. In this embodiment, the sensor adapter can be alternatively incorporated into a first end portion 530 of the cable 520, which would attach proximate to the monitor 502; a second end portion 540 of the cable 520, which would attach proximate to the sensor 506; or the cable body 522, as, for example, an attached molded cable block 550. Whether incorporated into the first end portion 530, second end portion 540 or the cable body 522, the adapter components are mounted to a substrate 515, as described.

If the sensor adapter is incorporated into the first end portion 530 or the second end portion 540, the substrate 515 with the adapter components is interconnected between the cable connector 522, 542 and the wiring within the cable body 522. If the sensor adapter is incorporated into the cable body 522, the substrate 515 is interconnected with the wiring within the cable body 522. Regardless, the substrate 515 is interconnected as described above with respect to the connector block 510. The substrate 515, connector 522, 542 and interconnection are then encapsulated to form a connector body 532, 542 or cable block body 552, also as described above.

As shown in FIG. 5, the sensor adapter may also be incorporated into the sensor 506. This, however, increases the cost of the sensor, which may be particularly critical for disposable sensors. For this embodiment, the adapter components can be mounted on a substrate 515, as described above. In turn, the substrate 515 can be mounted to the sensor 506, for example, by attaching and electrically interconnecting the substrate 515 to a flex circuit portion of the sensor 506. Alternatively, the adapter components can be mounted directly to the flex circuit portion of the sensor 506 or incorporated within particular sensor components, as with a conductive LED layer or encapsulant to form a coding or calibration resistor, as described below.

Figure 3:
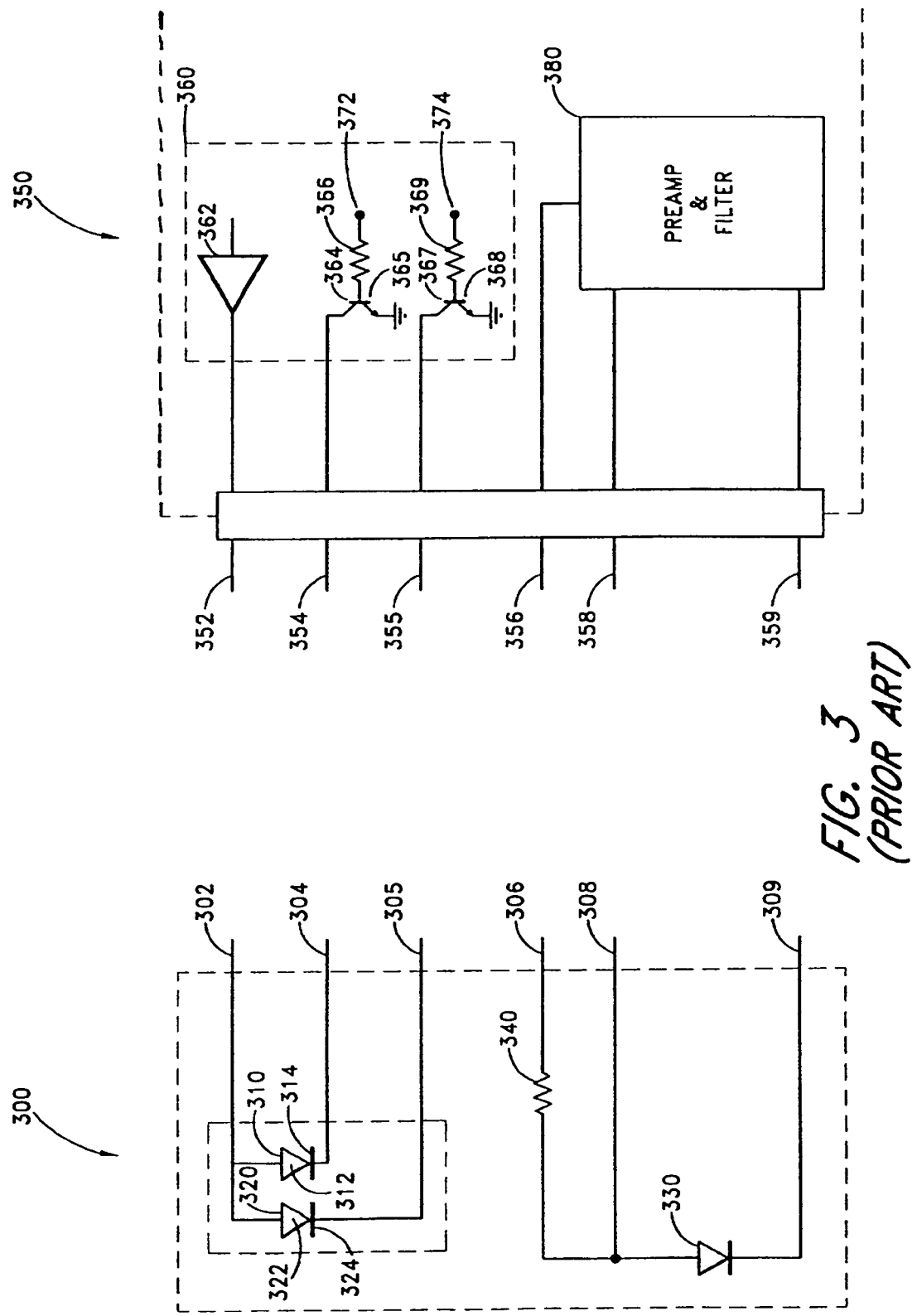
FIG. 3 is a schematic diagram representing yet another prior art sensor and corresponding monitor interface circuitry.
Figure 6:
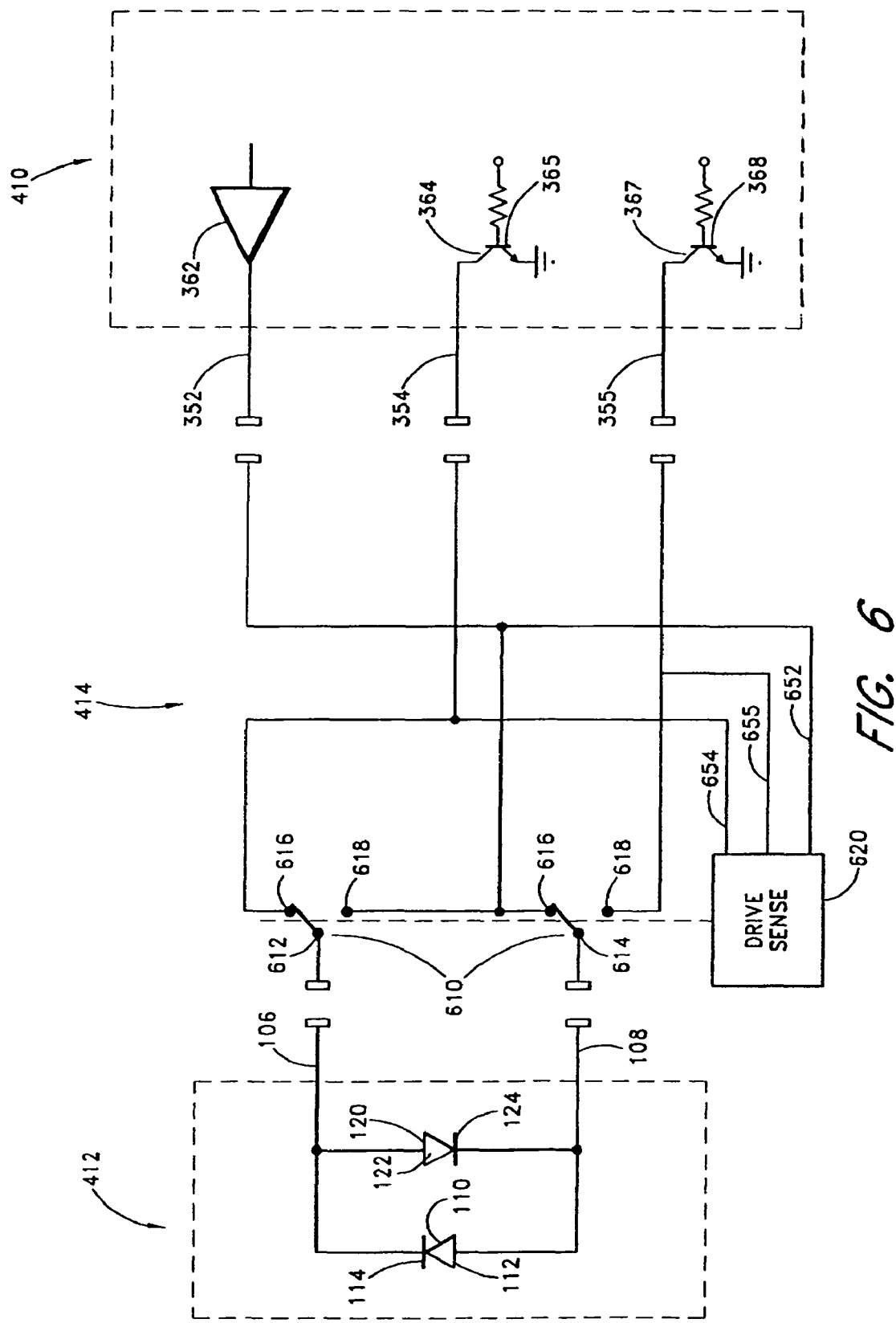
FIG. 6 is a block diagram of a drive configuration adapter portion of the sensor adapter for a monitor with three-wire, common-anode drivers to a sensor with two-wire, back-to-back LEDs.

FIG. 6 shows an embodiment of the light source configuration portion 414 of the sensor adapter. The light source portion 412 of the sensor is shown with a red LED 110 and infrared LED 120 in a back-to-back configuration. The light source driver portion 410 of the monitor is shown with a voltage source 362 and two current sinks 364, 367. This driver was described above with respect to FIG. 3 in connection with a common-anode LED sensor. Thus, the embodiment of the light source configuration element 414 shown in FIG. 6 adapts a three-wire common-anode driver to a two-wire, back-to-back LED light source. The discussion below is equally applicable to a sensor where the positions of the red LED 110 and the infrared LED 120 are swapped and, correspondingly, that of the red LED current sink 364 and infrared LED current sink 367 are swapped from that shown in FIG. 6.

As shown in FIG. 6, the adapter 414 has a double-pole, double-throw (DPDT) switch 610. A first switch pole 612 is connected to a first lead 106 of the sensor LEDs 110, 120. A second switch pole 614 is connected to a second lead 108 of the sensor LEDs 110, 120. In a first position 616 (depicted), the switch 610 connects the red LED anode 112 to the voltage source 362 and the red LED cathode 114 to the red LED current sink 364. In a second position 618 (not depicted), the switch 610 connects the infrared LED anode 122 to the voltage source 362 and the infrared LED cathode 124 to the infrared LED current sink 367. In this manner, the voltage source 362 is alternately switched between LED anodes 112, 122 and the appropriate current sink 364, 367 is alternately switched to the appropriate LED cathode 114, 124, alternately activating each of the LEDs 110, 120.

As illustrated in FIG. 6, the adapter also has a drive sense 620 that controls the switch 610. The drive sense 620 has a tap 652, 654, 655 on each of the monitor driver leads 352, 354, 355, which allows the drive sense 620 to determine which of the current sink transistors 365, 368 is biased to a conducting state. The drive sense 620 then sets the switch position accordingly. One will recognize many ways to implement the drive sense 620. For example, the output of a differential amplifier could control the switch 610, where the amplifier input is a resistor connected between the voltage source 362 and the red LED current sink 364. The amplifier could detect the voltage drop as current flows in the resistor when the red LED current sink 364 is in a conducting state, and actuate the switch 610 to the first position accordingly. When no voltage drop is detected, the switch 610 would return to the second position.

The switch 610 is implemented with active components, such as multiple FET transistors connected in a DPDT configuration and having a control voltage applied to the FET gates to control conduction through the FET channels, as is well-known in the art. One will also recognize that a number of FET transistor configurations are equivalent to the DPDT configuration shown in FIG. 6.

Figure 7:
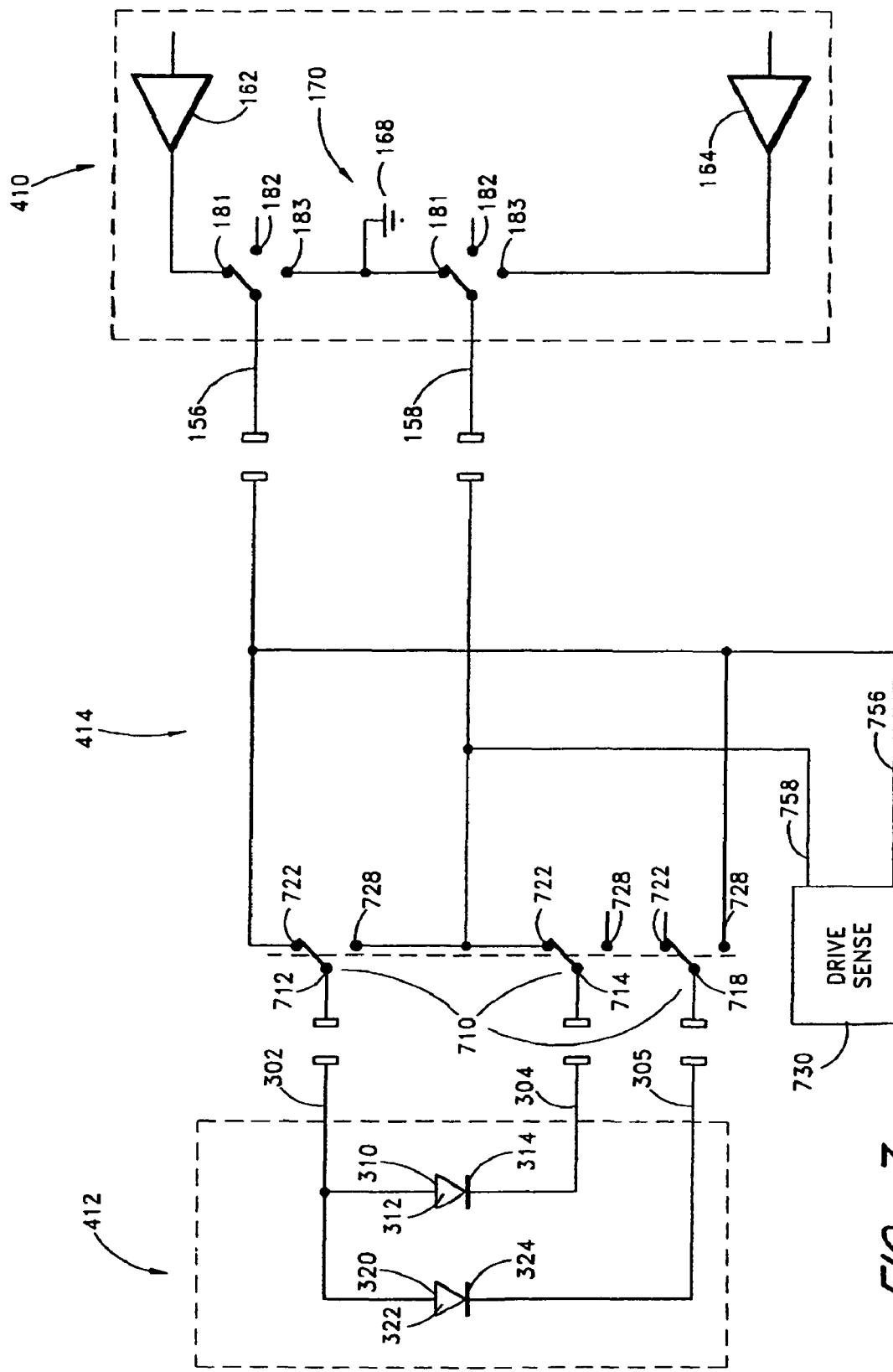
FIG. 7 is a block diagram of a drive configuration adapter portion of the sensor adapter for a monitor with two-wire, back-to-back LED drivers to a sensor with three-wire, common-anode LEDs.

FIG. 7 shows another embodiment of the light source configuration portion 414 of the sensor adapter. The light source portion 412 of the sensor is shown with a red LED 310 and infrared LED 320 in a three-wire, common-anode configuration. The light source driver portion 410 of the monitor is shown with two drivers 162, 164 and a DPDT switch 170. This driver was described above with respect to FIG. 1 in connection with a back-to-back LED sensor. Thus, the embodiment of the light source configuration element 414 shown in FIG. 7 adapts a two-wire, back-to-back LED driver 410 with a three-wire, common-anode LED light source 412.

As shown in FIG. 7, the adapter has a triple-pole, double-throw (3PDT) switch 710. A first switch pole 712 is connected to a first lead 302 of the sensor LEDs 310, 320. A second switch pole 714 is connected to a second lead 304 of the LEDs 310, 320. A third switch pole 718 is connected to a third lead 305 of the LEDs 310, 320. The adapter switch first position 722 corresponds to the driver switch first position 181, as depicted in FIG. 7. The adapter switch second position 728 corresponds to the driver switch third position 183. When the driver switch 170 is in the second position 182, the adapter switch 710 can be in either position 722, 728. In the first position 722, the adapter switch 710 connects the red LED anode 312 to a first monitor lead 156, when that lead 156 is connected to the red LED current source 162. In this first position 722, the switch 710 also connects the red LED cathode 314 to a second monitor lead 158, when that lead 158 is connected to ground 168. In this first position 722, the infrared LED cathode 324 is disconnected. In a second position 728, the adapter switch 710 connects the infrared LED anode 322 to the monitor second lead 158, when that lead 158 is connected to the infrared LED current source 164. In this second position 728, the adapter switch 710 also connects the infrared LED cathode 324 to the first monitor lead 156, when that lead 156 is connected to ground 168. In this second position 728, the red LED cathode 314 is disconnected. In this manner, the red LED current source 162 is driving the red LED 310 alternately as the infrared LED current source 164 is driving the infrared LED 320.

As illustrated in FIG. 7, the light source configuration portion 414 of the sensor adapter also has a drive sense 730 that controls the positions of the adapter switch 710. The drive sense 730 has a tap 756, 758 on each of the driver leads 156, 158 that allow the drive sense 730 to determine the position of the driver switch 170. The drive sense 730 then sets the sensor switch position accordingly. One will recognize many ways to implement the drive sense 730. For example, a differential amplifier could detect the polarity of the taps 756, 758, the amplifier output controlling the positions of the adapter switch 710. For example, the amplifier could detect that the polarity of the first monitor lead 156 is positive with respect to the second monitor lead 158, indicating the driver switch 170 is in the first position 181. The amplifier output would then actuate the adapter switch 710 to the first position 722. As discussed above with respect to FIG. 6, the switch is implemented with active components, for example, FET transistors. Also, as discussed above, one will also recognize that a number of FET transistor configurations would be equivalent to the 3PDT configuration shown in FIG. 7.

Figure 8:
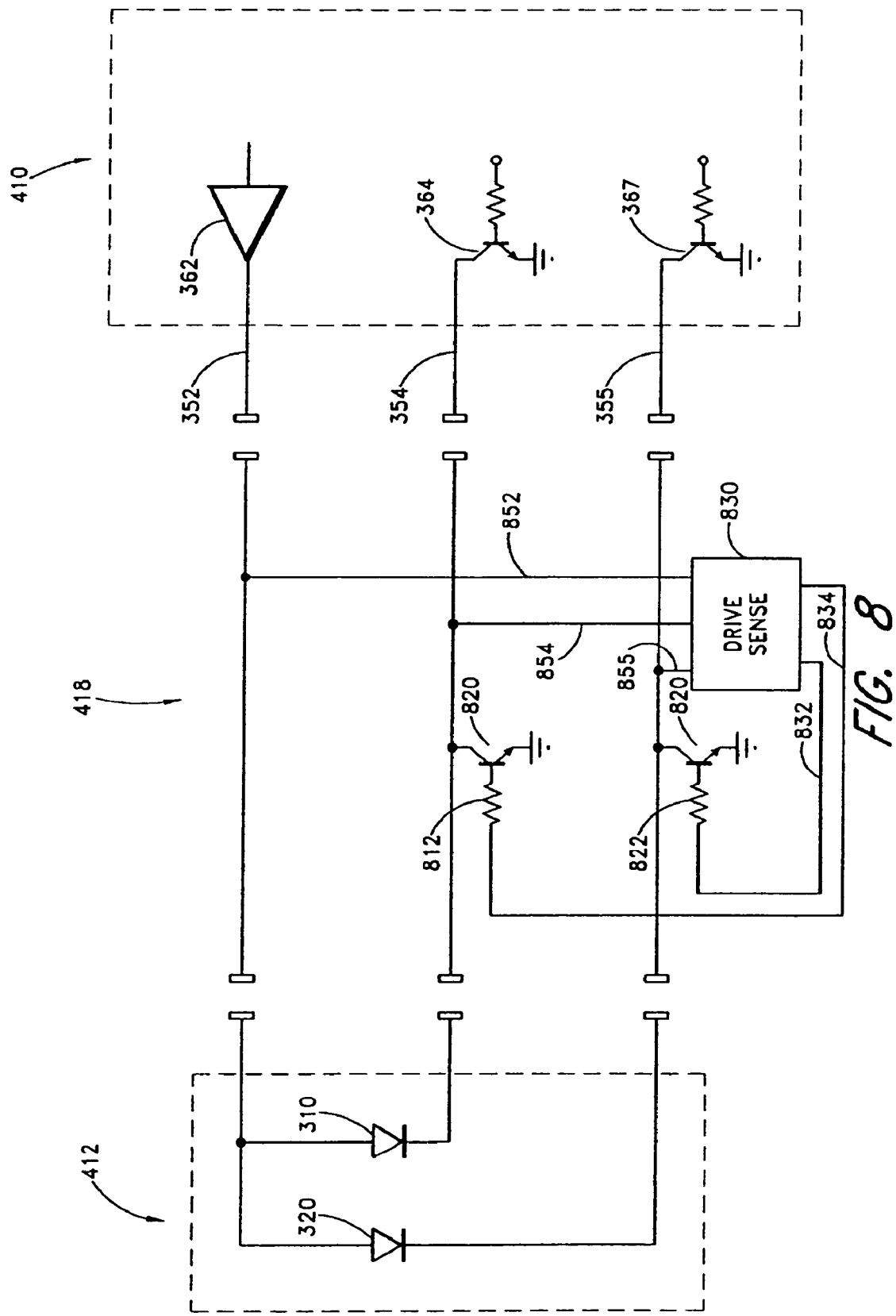
FIG. 8 is a block diagram of a drive limit adapter portion of the sensor adapter illustrating a drive current gain.

FIG. 8 shows an embodiment of the drive limit portion 418 of the sensor adapter. In this embodiment, the drive limit adapter 418 provides increased drive current through the sensor light source 410. For purposes of illustration, the sensor light source 410 shown in FIG. 8 is a three-wire, common-anode LED configuration as described above with respect to FIG. 3. Also for purposes of illustration, the monitor light source driver 412 is configured to drive a three-wire, common-anode LED configuration, also as described above with respect to FIG. 3. It is assumed, however, that the sensor LEDs 310, 320 require an increased drive current over what the driver 412 provides. The drive limit adapter portion 418, therefore, provides an adapter red LED current sink 810 in parallel with the monitor red LED current sink 364 and an adapter infrared LED current sink 820 in parallel with the monitor infrared LED current sink 367. A drive sense 830 similar to the one described above with respect to FIG. 6 controls the adapter current sinks 810, 820. That is, the drive sense 830 has a tap 852, 854, 855 on each of the driver leads 352, 354, 355 that allow the drive sense 830 to determine which of the monitor current sinks 364, 367 are biased to a conducting state. The drive sense 830 then biases the corresponding adapter current sink 810, 820 to a conducting state. The bias resistors 812, 822 and the bias voltage applied by the drive sense control outputs 832, 834 determine the current through the adapter current sinks 810, 820. The current through the red LED 310 is the sum of the current through the corresponding adapter red LED current sink 810 and the monitor red current sink 364. Likewise, the current through the infrared LED 320 is the sum of the current through the corresponding adapter infrared LED current sink 820 and the monitor infrared current sink 367.

Figure 9:
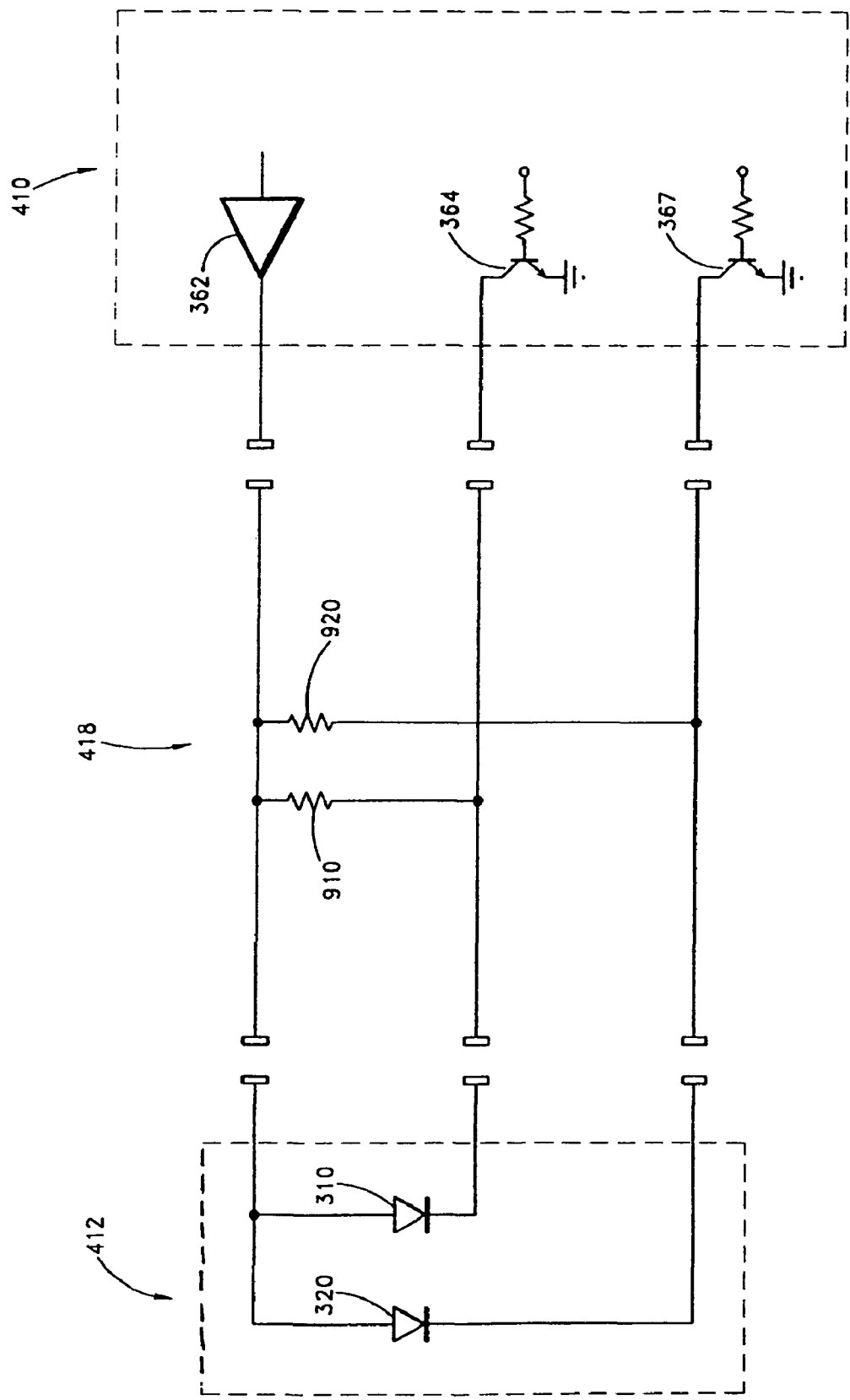
FIG. 9 is a block diagram of a drive limit adapter portion of the sensor adapter illustrating a drive current reduction.

FIG. 9 shows another embodiment of the drive limit portion 418 of the sensor adapter. In this embodiment, the drive limit adapter 418 provides for decreased drive current through the sensor light source 410. For purposes of illustration, the sensor light source 410 and the monitor driver 412 are shown the same as described above with respect to FIG. 8. For this embodiment, however, it is assumed that the sensor LEDs 310, 320 require a reduced drive current from what the driver 412 provides. The drive limit adapter 418, therefore, provides a red LED shunt 910 and an infrared LED shunt 920. Each shunt 910, 920 allows an amount of current to bypass a particular LED 310, 320, as determined by the resistance value of the shunt 910, 920. The current through the red LED 310 is the difference between the current drawn by the red LED current sink 364 and the current bypassed through the red LED shunt 910. Likewise, the current through the infrared LED 320 is the difference between the current drawn by the infrared LED current sink 367 and the current bypassed through the infrared LED shunt 920.

Figure 10:
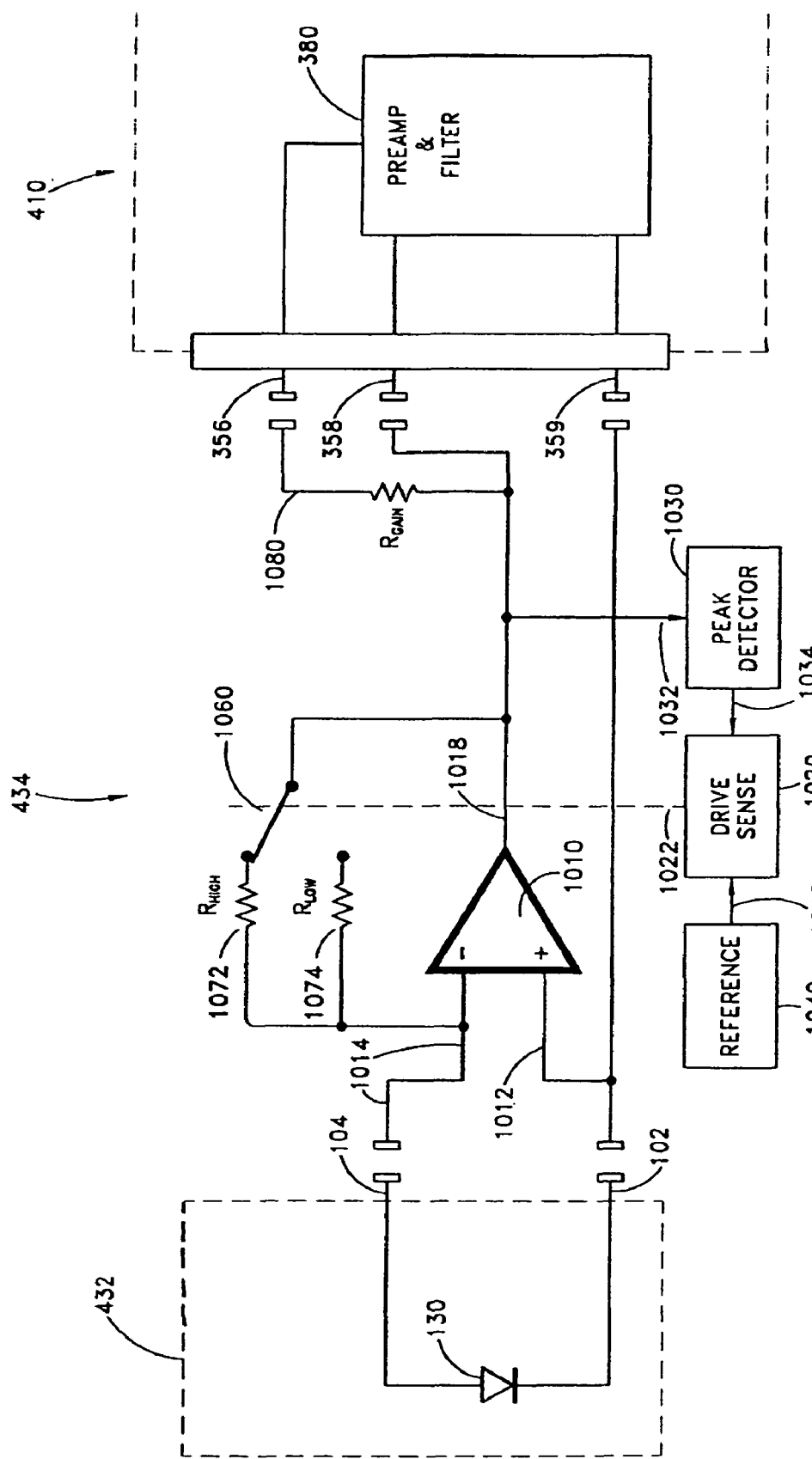
FIG. 10 is a block diagram illustrating the active gain adapter portion of the sensor adapter.

FIG. 10 depicts an embodiment of the active gain portion 434 of the sensor adapter. Active gain 434 adapts the light detector portion 432 of the sensor to the signal conditioner portion 430 of the monitor. One function of the active gain adapter 434 is to provide a resistor 1080 in the feedback path 356 of a preamplifier 380, for monitors which require this feature to control dynamic range, as described above with respect to FIG. 3. The value, $R_{gain}$, of the resistor 1080 determines the gain of the preamplifier 380. As illustrated in FIG. 10, another function of the active gain adapter 434 is to adjust the signal level of the photodiode 130. This function also adapts the dynamic range of the monitor preamplifier 380 to a particular sensor type or application. A variable gain amplifier 1010 adjusts the detected signal level from the photodiode 130. The amplifier inputs 1012, 1014 are connected to the photodiode output leads 102, 104. The amplifier output 1018 drives the preamplifier input 358. A single-pole, double-throw (SPDT) gain switch 1060 selects one of two feedback resistors 1072, 1074. The selected resistor value, $R_{high}$ or $R_{low}$, determines the amplifier gain.

The gain switch 1060 is controlled by a comparator 1020 in combination with a peak detector 1030 and a reference 1040. The peak detector 1030 has an input 1032 connected to the output 1018 of the amplifier 1010. The peak detector 1030 measures the amplified difference between detector dark current and detector signal current. This difference at the peak detector output 1034 is compared 1020 to a reference output 1042. If the peak signal level is below the reference value, the comparator output 1022 actuates the gain switch 1060 to select the high gain resistor 1072. If the peak signal level is above the reference value, the comparator output 1022 actuates the gain switch 1060 to select the low gain resistor 1074. Hysteresis or integration of the peak detector output, for example, can be used to stabilize the amplifier gain settings, as is well-known in the art. Also, one will recognize that a bank of N resistors and single-pole, N-throw switch can be used to provide multiple gain settings for the amplifier 1010, as determined by multiple reference outputs from the reference source 1040.

Figure 11:
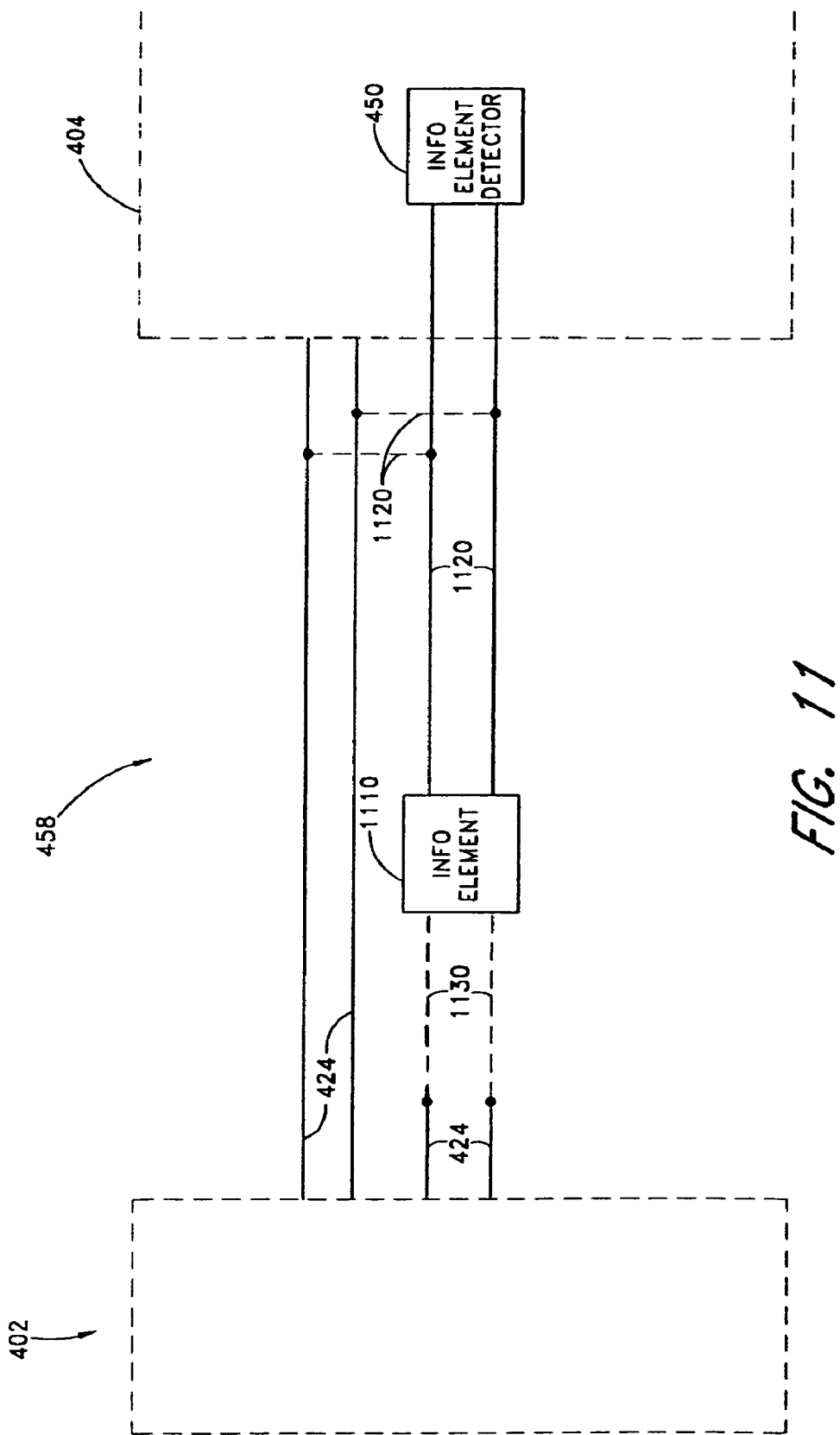
FIG. 11 is a schematic of an embodiment of the information generator adapter portion of the sensor adapter featuring an adapter information element.

FIG. 11 illustrates an embodiment of the information generator portion 458 of the sensor adapter. An information element 1110 is located in the sensor adapter to substitute for an equivalent sensor information element. The information element 1110 connects via conductors 1120 to the information element detector portion 450 of the monitor 404, which senses the information content of the information element 1110. The information element 1110 may have series connections 1130 or parallel connections 1140 to outputs 424 of the sensor 402.

As an example, the sensor adapter could be an adapter cable having a coding or calibration resistor mounted as described above with respect to FIG. 5. In particular, as illustrated with the monitor 250 of FIG. 2, the adapter cable could have an information element that is a calibration resistor, which connects between the monitor leads 256, 258. Similarly, as illustrated with the monitor 150 of FIG. 1, the adapter cable could have an information element that is a coding resistor, which connects between the monitor leads 156, 158. In this manner, a sensor without a coding or calibration resistor would properly function when attached with the adapter cable to a monitor that requires such a resistor.

Figure 1:
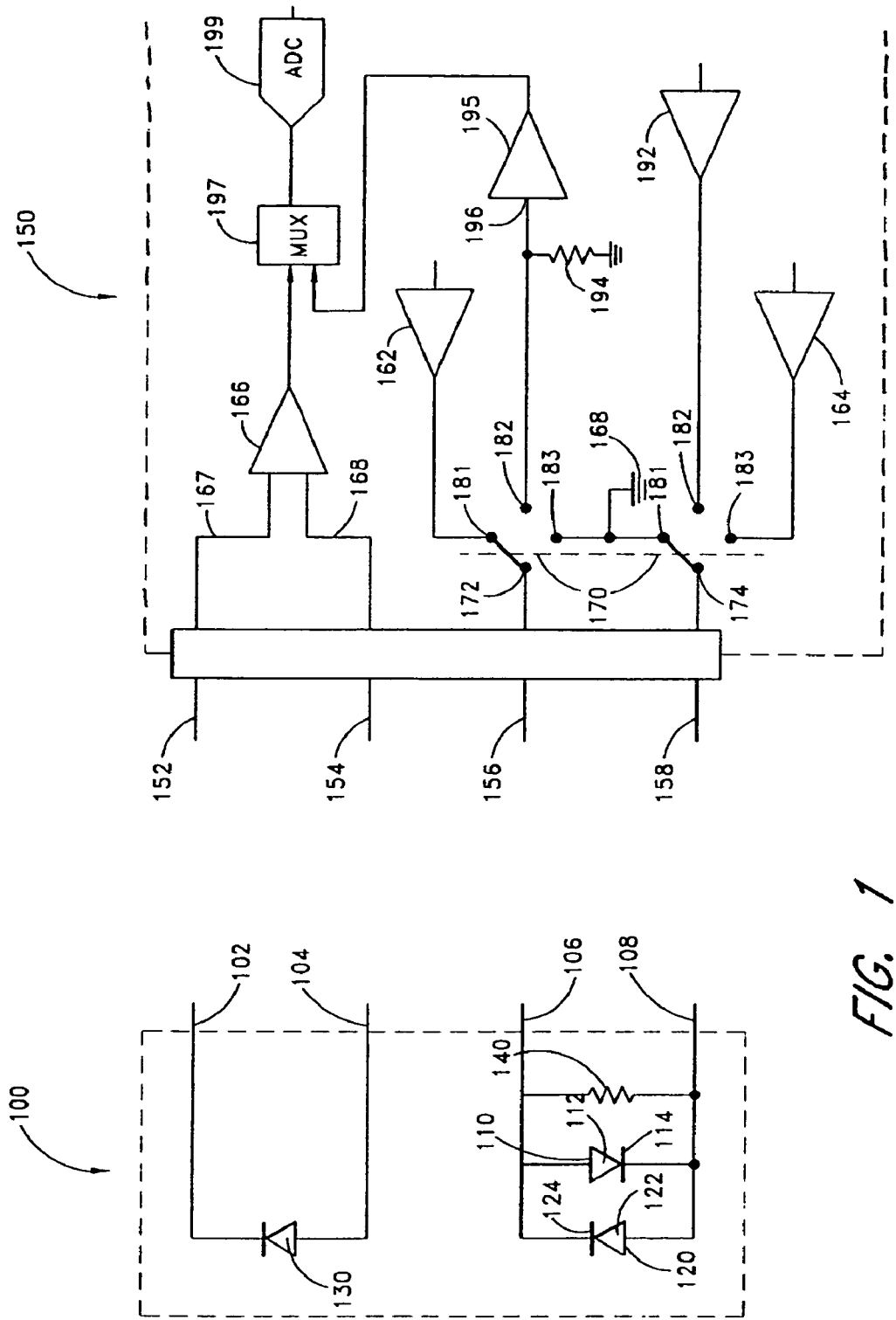
FIG. 1 is a schematic diagram representing a sensor and corresponding monitor interface circuitry.
Figure 2:
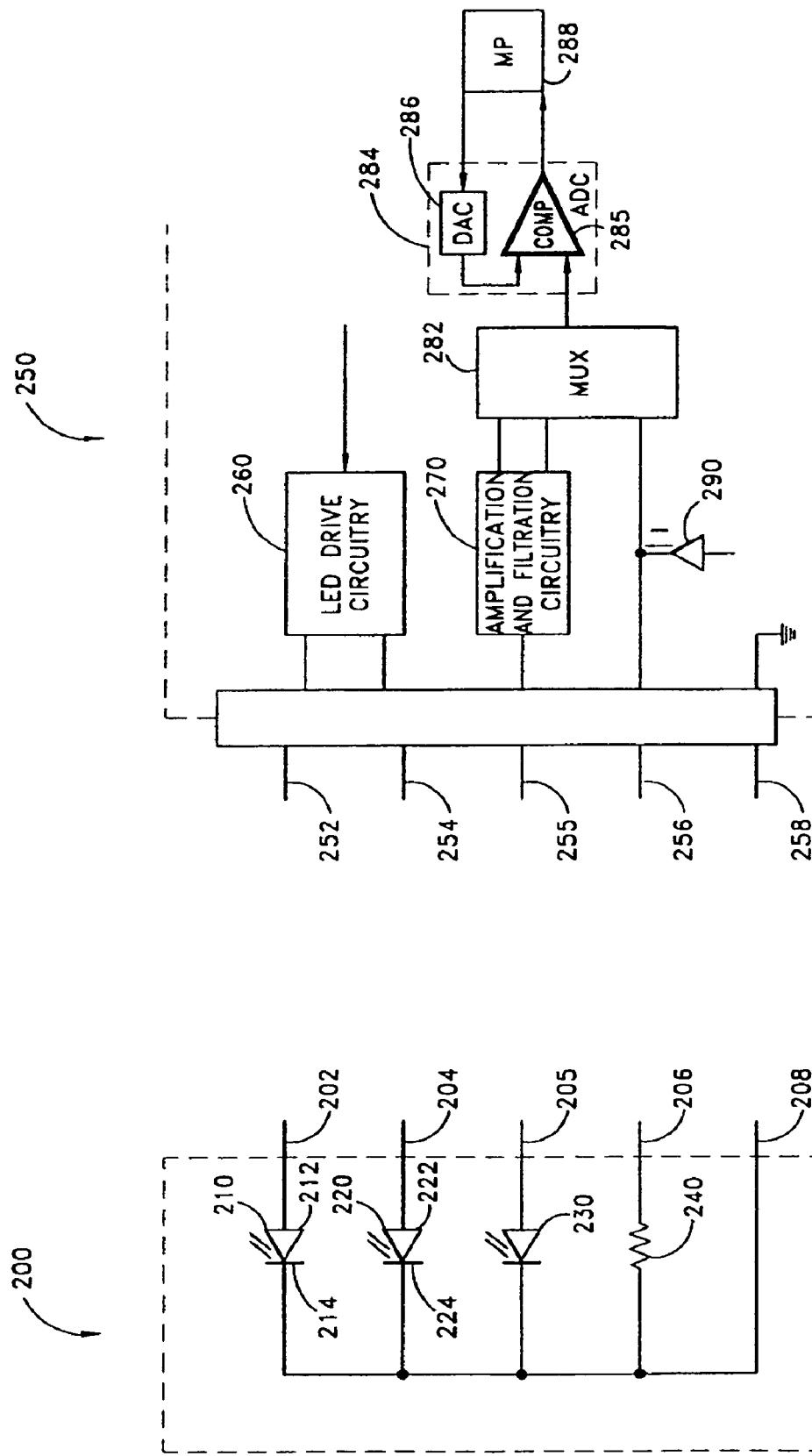
FIG. 2 is a schematic diagram representing another prior art sensor and corresponding monitor interface circuitry.

As illustrated in FIG. 1, an equivalent substitute for a calibration or coding resistor can also be located on the sensor itself in the form of leakage resistance built into the sensor. In one embodiment, the red LED 110 and infrared LED 120 can be encapsulated with a material having some conductance so as to form an equivalent resistance equal to the desired value of the coding resistor 140. In another embodiment, the semiconductor material of the red LED 110, the infrared LED 120 or both can be fabricated with some conductance to form an equivalent resistance equal to the desired value of the coding resistor 140.

Figure 12:
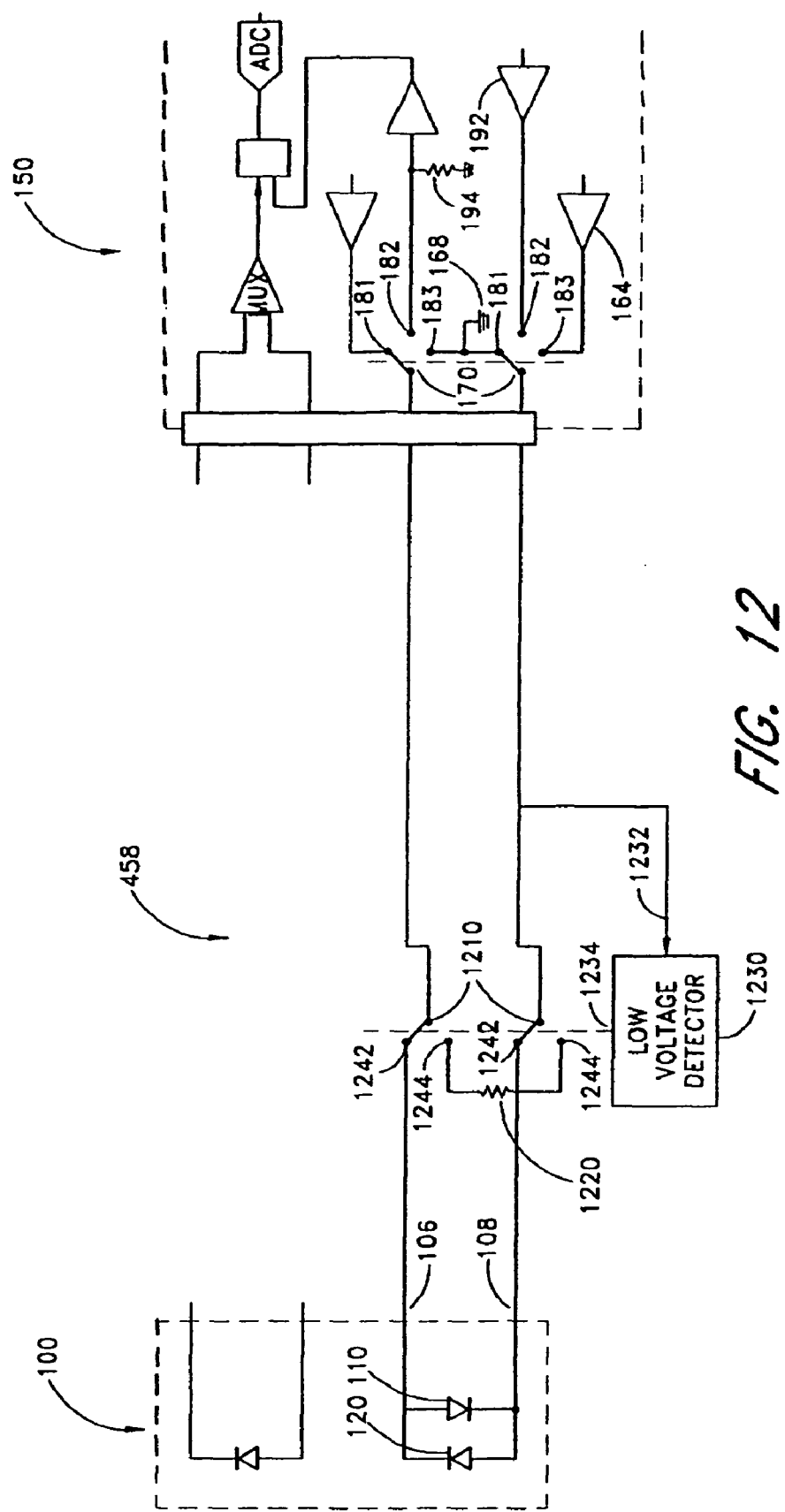
FIG. 12 is a schematic of another embodiment of the information generator adapter portion of the sensor adapter.

FIG. 12 illustrates another embodiment of the information generator portion 458 of the sensor adapter. The information generator 458 has a DPDT adapter switch 1210, an adapter resistor 1220 and a low-voltage detector 1230. The adapter switch 1210 has a first position 1242 that connects the sensor LED leads 106, 108 to the monitor output leads 156, 158. The adapter switch 1210 has a second position 1244 that connects the adapter resistor 1220 across the output leads 156, 158. The low-voltage detector 1230 has an input 1232 that can be connected to the low-voltage output lead 158. The low-voltage detector 1230 has an output that controls the adapter switch 1210.

As illustrated in FIG. 12, the operation of the information generator 458 is illustrated with respect to the monitor 150, described above with respect to FIG. 1. In its first position 1242, the adapter switch 1210 connects the two leads of the sensor LEDs 106, 108 to the two monitor output leads 156, 158. The adapter switch first position 1242 corresponds to the monitor switching circuit first position 181 and third position 183, at which the LED drivers 162, 164 alternately activate the LEDs 110, 120.

As shown in FIG. 12 and described above with respect to FIG. 1, during calibration, the switching circuit 170 is set to a second position 182 which isolates the monitor output leads 156, 158 from the drivers 162, 164 and ground 168. During this calibration period, a combination of a low-voltage source 192 and a reference resistor 194 are connected to the output leads 156, 158 to determine the value of a sensor coding resistor. The low voltage detector 1230 senses the low voltage on the output leads 156 and actuates the adapter switch 1210 to its second position 1244. With the adapter switch 1210 in the second position 1244, the adapter resistor 1220 is connected between to the low-voltage source 192 and the reference resistor 194. As a result, the monitor reads the value of the adapter resistor 1220, which is a predetermined resistance equivalent to the value of a coding resistor required by the monitor 150 for proper operation. In this manner, the information generator 458 adapts a sensor 100 without a coding resistor 140 to the monitor 150.

Figure 13:
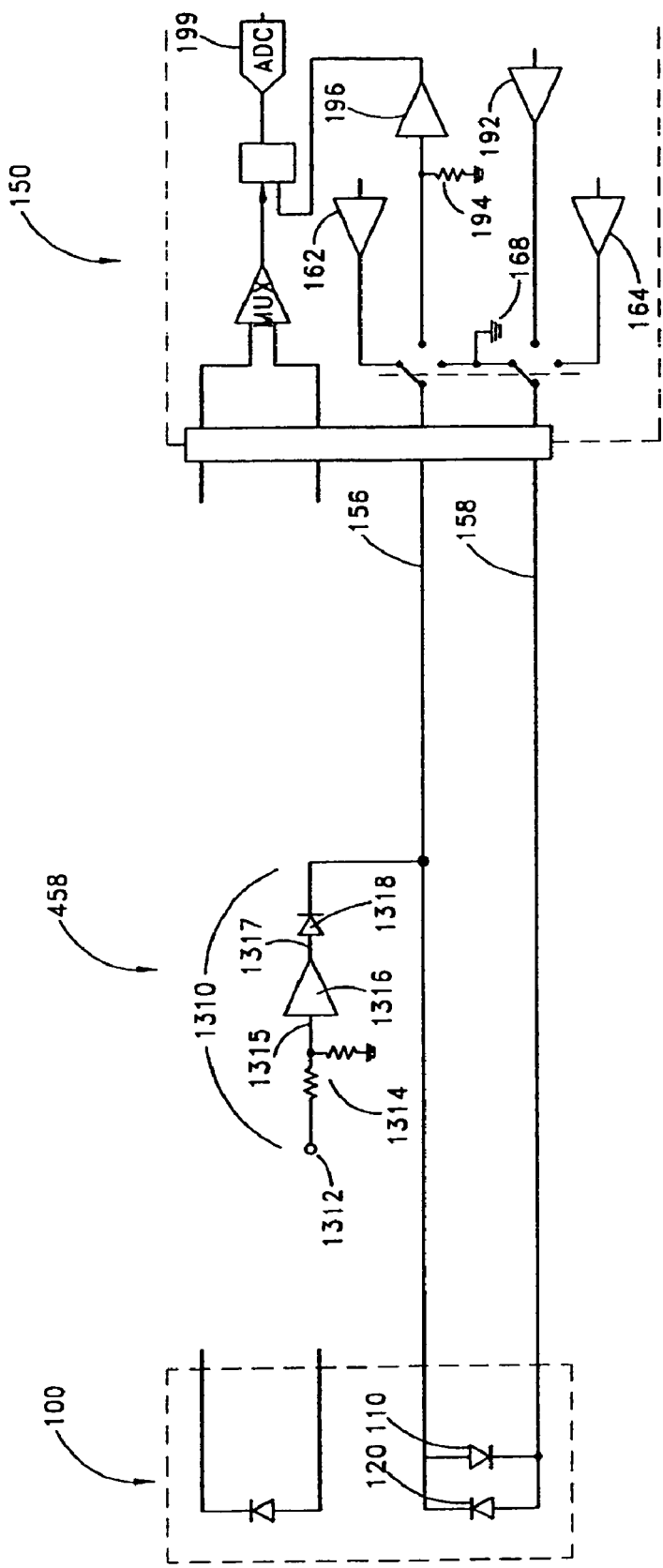
FIG. 13 is a schematic of yet another embodiment of the information generator adapter portion of the sensor adapter.

FIG. 13 illustrates yet another embodiment of the information generator portion 458 of the sensor adapter. The information generator 458 comprises a fixed voltage source 1310 connected to the output lead 156 of the reference resistor 194. The voltage source 1310 has a bias voltage input 1312 and, bias resistors 1314, which divide the voltage between the bias voltage input 1312 and the input 1315 of the buffer amplifier 1316. The output 1317 of the amplifier 1316 is connected to the anode of an isolation diode 1318, the cathode of which is connected to the output lead 156. While the LEDs 110, 120 are driven, the isolation diode 1318 is back biased by the red LED driver 162 or by the combination of the infrared LED driver 164 and the infrared LED 120 voltage drop, effectively isolating the fixed voltage source 1310 from the output lead 156.

During the initialization interval described above, the monitor 150 is expecting to read a coding resistor of value $$R_c = R_{ref} \cdot [(V_{low}/V_{adc}) - 1],$$

where $R_{ref}$ is the resistance of the monitor reference resistor 194, $V_{low}$ is the output voltage of the low-voltage source 192 and $V_{adc}$ is the voltage measured at the buffer input 196 and also output to the ADC 199. The LEDs 110, 120 are not conducting during the calibration period because the red LED 110 is back biased and the low-voltage source 192 provides insufficient forward voltage to the infrared LED 120 for conduction to occur. Because the sensor 100 does not have a coding resistor, the low-voltage source 192 is effectively isolated from the output lead 156 and reference resistor 194. During this period, the isolation diode 1318 is forward biased by the amplifier 1317. As a result, the voltage at the amplifier output 1317, ignoring the diode voltage drop, appears across the reference resistor 194. If the predetermined value of the voltage source is $$V = V_{low} \cdot [R_{ref}/(R_c + R_{ref})],$$

The voltage at the buffer input 196 is the same as if the sensor had a coding resistor of value, $R_c$, as can be seen by substituting V for $V_{adc}$ in the equation for $R_c$ above. Thus, the fixed voltage source provides equivalent information to the monitor 150 as if the sensor 100 had a coding resistor. One will recognize that other voltage source configurations are possible. Further, an equivalent current source can be connected to the output lead 156 to simulate a sensor coding resistor. The predetermined value of that current source is:

$$I = V_{low}/(R_c + R_{ref})$$

This current flows through the reference resistor 194 such that the voltage read by the monitor, $V_{adc}$ at the ADC 199, is the same as given above for the voltage source embodiment.

Figure 14:
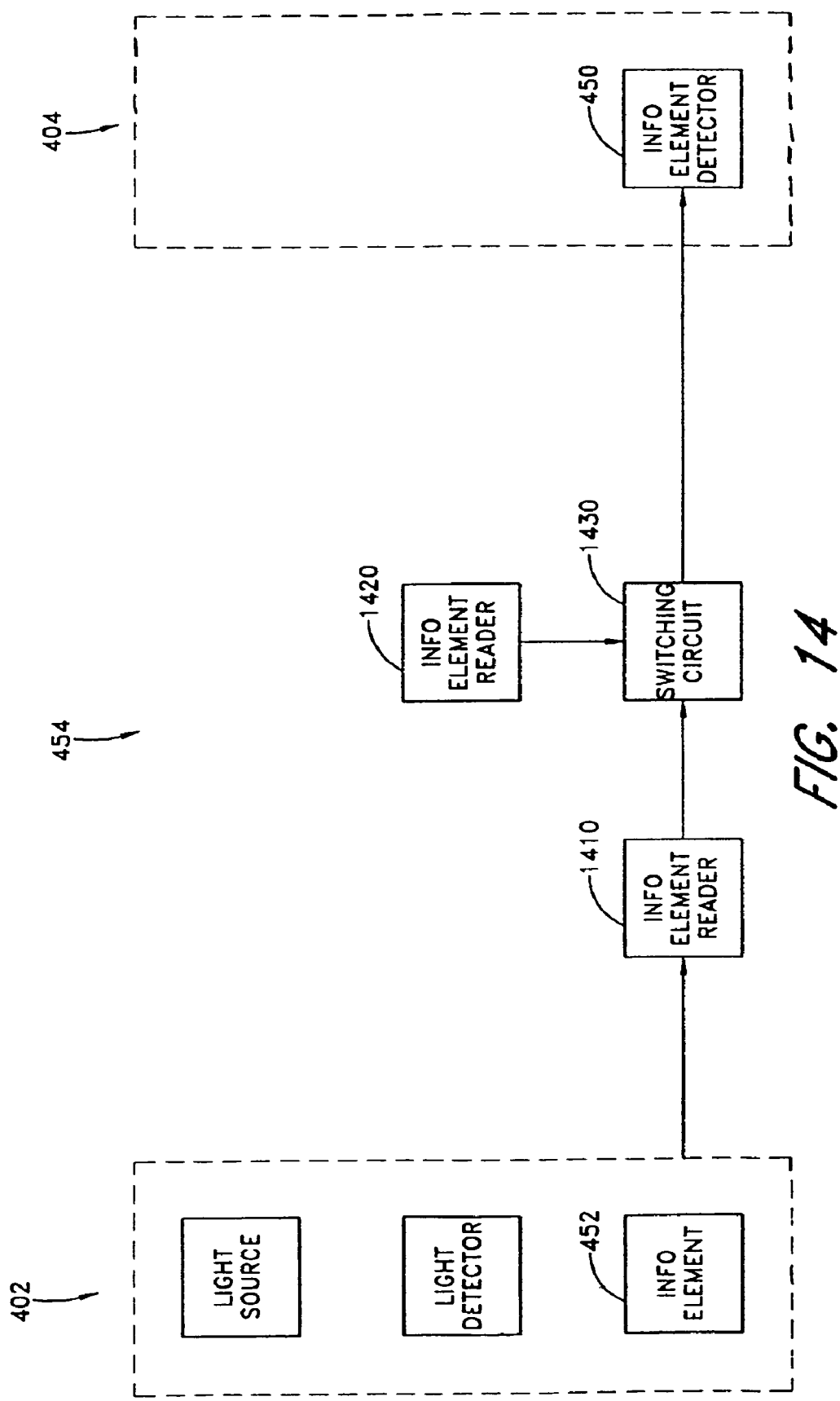
FIG. 14 is a schematic diagram of the information translation adapter portion of the sensor adapter.

FIG. 14 illustrates an embodiment of the information translator portion 454 of the sensor adapter. The information translator 454 reads a sensor information element 452 and provides an equivalent value, i.e. a translated value providing the same information, to the information element detector portion 450 of a monitor 404. The translator 454 has an information element reader 1410 that determines the sensor information, e.g. sensor type, manufacturer, calibration data, or security code from a sensor information element 452. The translator 454 also has an information element array 1420. The array 1420 is a predetermined set of different information elements that correspond to the possible sensors that the monitor 404 accepts. At least one information element is selected from the array 1420 and connected to the information element detector 450, as determined by a switching circuit 1430. The information element reader 1410 controls the state of the switching circuit 1430. In this manner, the information element reader 1410 can determine the sensor information element value, select an equivalent value from the information element array 1420, and actuate the switching circuit 1430, thereby connecting the corresponding element or elements from the array 1420 to the monitor information element detector 450.

Figure 15:
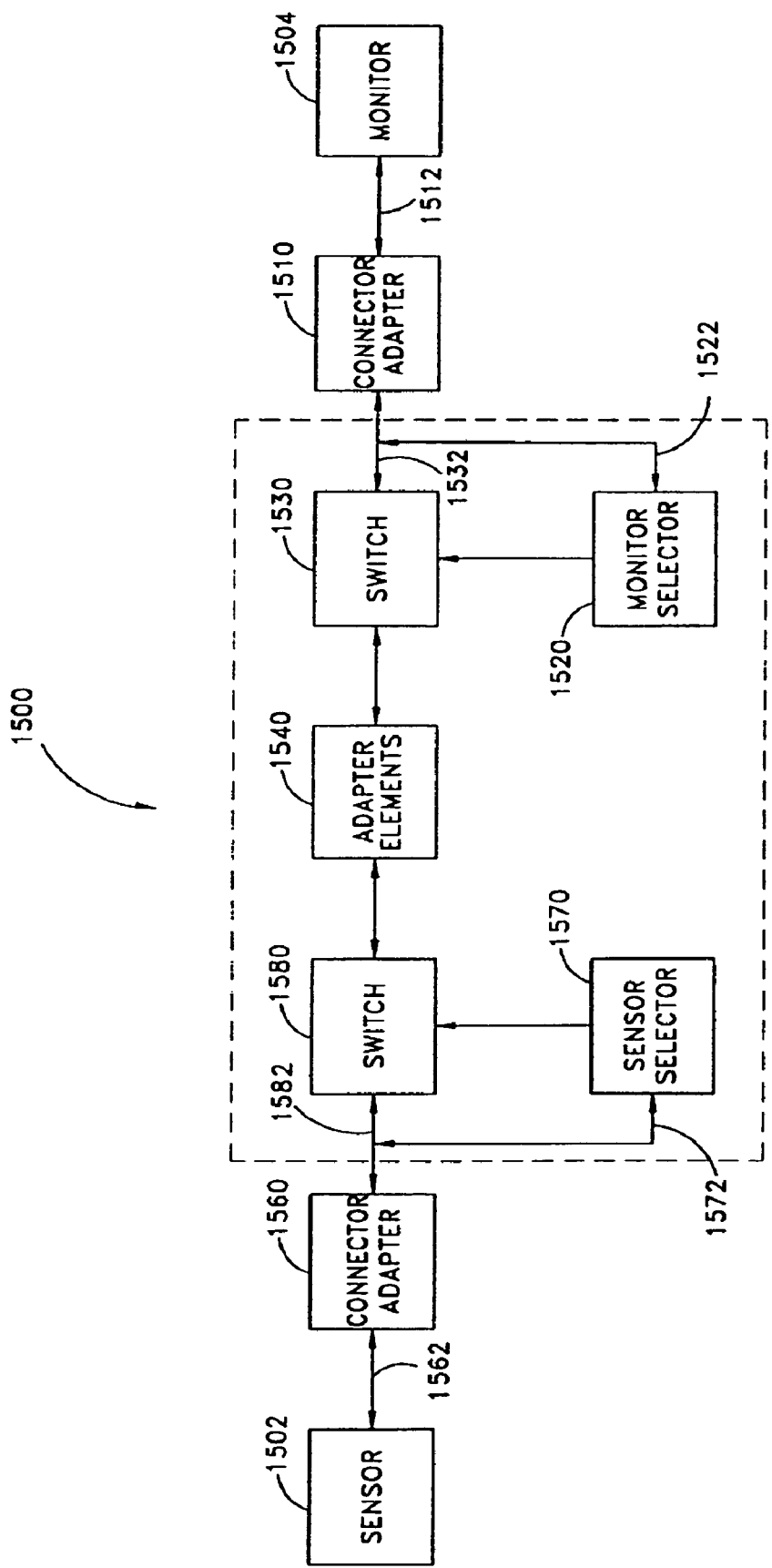
FIG. 15 is a block diagram of a universal sensor adapter embodiment of the sensor adapter.

FIG. 15 shows an embodiment of a sensor adapter which incorporates a combination of the adapter elements described above in addition to other elements described in detail below to create a universal adapter 1500. In general, the universal adapter 1500 allows one sensor 1502 from a variety of possible sensors to be connected to one monitor 1504 from a variety of possible monitors to create a pulse oximetry system. The universal adapter 1500 has a first connector adapter 1510, a monitor selector 1520, a first switch 1530 and a number of adapter elements 1540. These components allow the universal adapter 1500 to sense the electrical characteristics of the monitor 1504, such as the drive configuration and drive levels, and to select the necessary adapter elements 1540 accordingly. The universal adapter 1500 also has a second connector adapter 1560, a sensor selector 1570, and a second switch 1580. These components allow the universal adapter to sense the electrical characteristics of the sensor 1502, such as LED configuration and information element presence and to select the necessary adapter elements 1540 accordingly.

Figure 16:
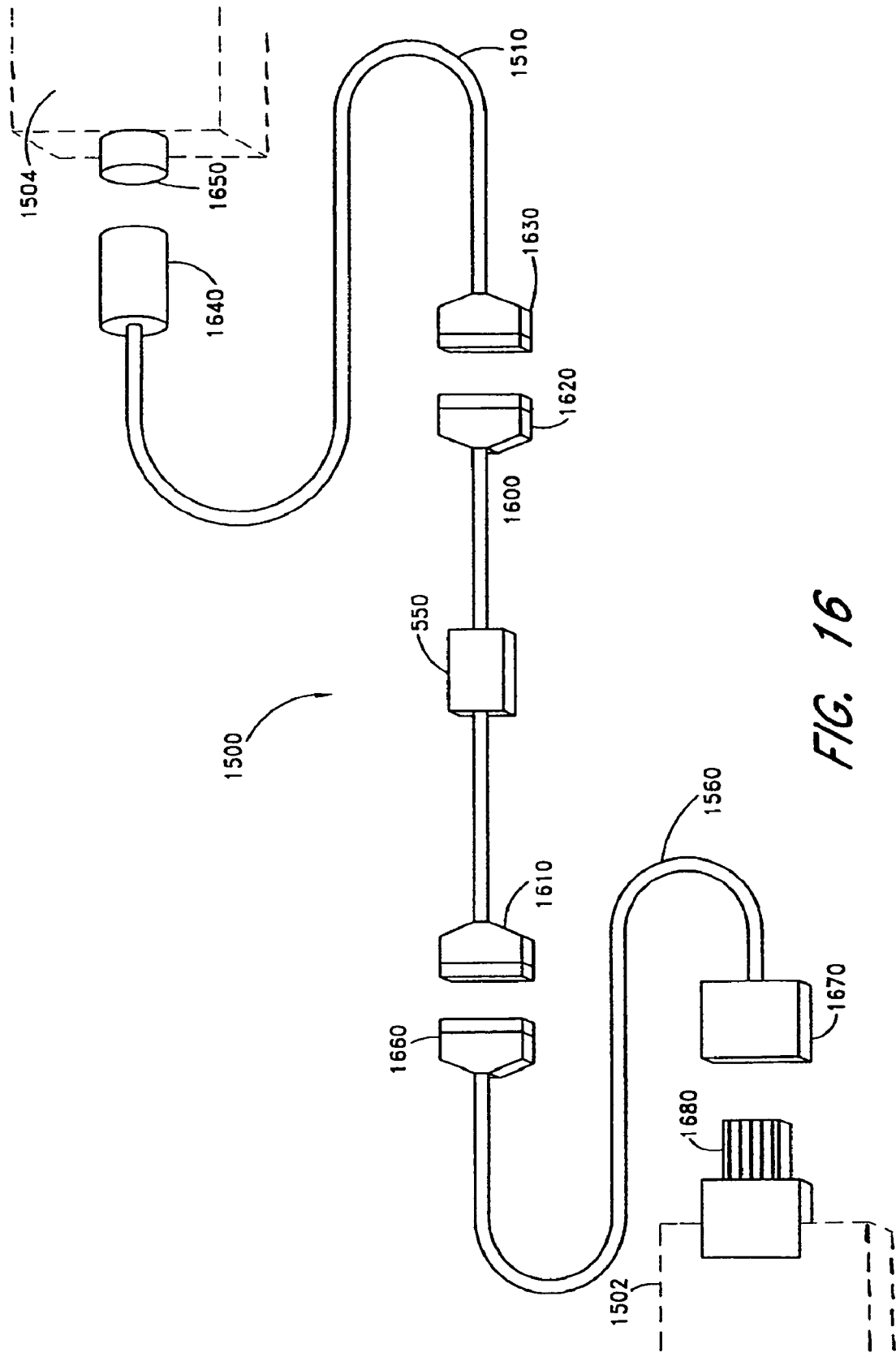
FIG. 16 is an illustration of a universal adapter cable embodiment of the universal sensor adapter.

FIG. 16 further illustrates the universal adapter 1500 described above with respect to FIG. 15. The universal adapter 1500 is shown as a sensor adapter cable 1600 having generic connectors 1610, 1620 at either end of the cable 1600. Attached to the cable and electrically connected to the cable wiring is an molded cable block 550 as described above with respect to FIG. 5. The cable block contains the adapter components 1520, 1530, 1540, 1570, 1580 shown in FIG. 15.

As illustrated in FIG. 16, a first connector adapter 1510 is a conventional adapter cable having a connector 1630 at one end which mates with the generic connector 1620 of the sensor adapter cable 1600. A connector 1640 at the other end of the connector adapter 1510 is the specific connector which mates with a particular monitor connector 1650. The cable wiring of the connector adapter 1510 is cross-wired between the end connectors 1630, 1640 as necessary to match the predetermined pinouts of the connector 1620 of the sensor adapter cable 1600 to the pinouts of the connector 1650 of the monitor 1504. In this manner, the first connector adapter 1510 accommodates a variety of physical connectors and pinouts of various monitors 1504.

Likewise, a second connector adapter 1560 is a conventional adapter cable having a connector 1660 at one end which mates with the generic connector 1610 of the sensor adapter cable 1600. A connector 1670 at the other end of the connector adapter 1560 is the specific connector 1670 which mates with a particular sensor connector 1680. The cable wiring of the connector adapter 1560 is cross-wired between the end connectors 1660, 1670 as necessary to match the predetermined pinouts of the connector 1610 of the sensor adapter cable 1500 to the pinouts of the connector 1680 of the sensor 1502. In this manner, the second connector adapter 1560 accommodates a variety of physical connectors and pinouts of various sensors 1502. The sensor adapter cable 1600, as described above, is advantageously of a single design having generic connectors 1610, 1620 with predetermined signal pinouts that mate with each of a family of specific adapter cables 1510, 1560 manufactured to match specific sensors 1502 and specific monitors 1504.

As illustrated in FIG. 15, the signal lines 1532 between the first switch 1530 and the connector adapter 1510 have branches 1522 to the monitor selector 1520. Because the pinouts of the universal adapter 1500 are predetermined, it is known which of these signal lines 1532 correspond to particular monitor leads 1512. Thus, the monitor selector 1520 tests these signal lines 1532 to determine the signal characteristics of an attached monitor 1504, as described in more detail below with respect to FIG. 17. Once the signal characteristics for the monitor 1504 are determined, the output 1524 of the monitor selector 1520 controls the first switch 1530 to connect the signal lines 1532 to corresponding adapter element 1540.

Likewise, the signal lines 1582 between the second switch 1580 and the connector adapter 1560 have branches 1572 to the sensor selector 1570. Because the pinouts of the universal adapter 1500 are predetermined, it is known which of these signal lines 1582 correspond to particular sensor leads 1562. Thus, the sensor selector 1570 tests these signal lines 1582 to determine the signal characteristics of an attached sensor 1502, as described in more detail below with respect to FIG. 17. Once the signal characteristics for the sensor 1502 are determined, the output 1574 of the sensor selector 1570 controls the second switch 1580 to connect the signal lines 1582 to corresponding ones of the adapter elements 1540.

Figure 17:
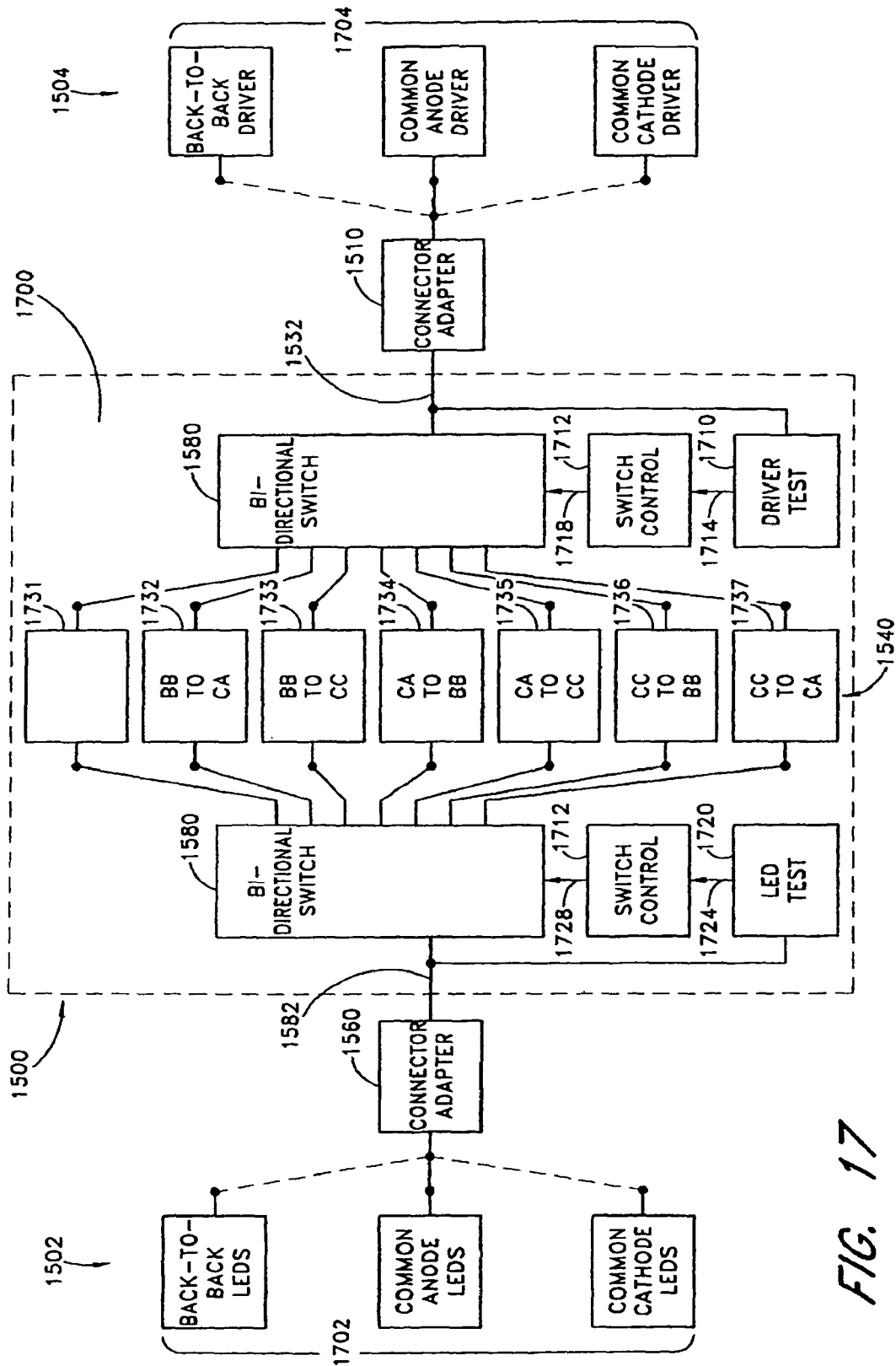
FIG. 17 is a block diagram of the configuration adapter portion of the universal sensor adapter.

FIG. 17 illustrates an embodiment for a configuration portion 1700 of the universal adapter 1500 that matches the monitor driver 1704 to the sensor LEDs 1702. This configuration portion 1700 has a driver test 1710 and a switch control 1712. The driver test 1710 senses the driver configuration from the monitor signal lines 1532 and provides an output 1714 to the switch control 1712. The switch control 1712 has inputs from the driver test output 1714 and the LED test output 1724 and provides a control output 1718 that causes a first bi-directional switch 1530 to connect the monitor driver 1704 to the corresponding adapter elements 1731-1737. That is, the first switch is equivalent to a bi-directional one-line to seven-line multiplexer.

The configuration portion 1700 also has an LED test 1720. The LED test 1720 senses the LED configuration from the sensor signal lines 1582 and provides an output 1724 to the switch control 1712. The switch control 1712 has inputs from the LED test output 1724 and the driver test output 1714 and provides a control output 1728 that causes a second bi-directional switch 1580 to connect the sensor LEDs 1702 to the corresponding adapter elements 1731-1737. The second switch 1580 is equivalent to the first switch 1530. The adapter elements comprise adapters 1732-1737 for all six combinations of drivers and incompatible sensor configurations. In addition, there is a "straight-through" adapter 1731 for the case of matching drivers and sensor LEDs, e.g. back-to-back driver 1704 and back-to-back LEDs 1702.

As illustrated in FIG. 17, it is assumed that a monitor 1504 has three possible drivers 1704. That is, an attached monitor will have circuitry for driving either back-to-back LEDs, common-anode LEDs or common-cathode LEDs. Thus, the configuration adapter 1700 has three signal lines 1532 from the monitor driver 1704. For example, as illustrated in FIG. 6, a common-anode driver 410 has three leads 352, 354, 355 that correspond to the three signal lines 1532. As illustrated in FIG. 7 as another example, a back-to-back driver 410 has two leads 156, 158 which would correspond to two of the three signal lines 1532, leaving one of the three signal lines 1532 unused.

FIG. 18 illustrates an embodiment of the driver test 1710. The driver test 1710 looks at the three signal lines 1532 to determine the driver configuration. The drive test circuit 1710 shown has three differential amplifiers 1810, 1820, 1830, each with inputs across a unique pair of the three signal lines 1532. That is, a first amplifier 1810 senses a signal on a first pair of signal lines 1802, 1804, a second amplifier 1820 senses a signal on a second pair of signal lines 1802, 1805, and a third amplifier 1830 senses a signal on a third pair of signal lines 1804, 1805.

If a monitor driver is configured for back-to-back LEDs, then, as illustrated in FIG. 7, the equivalent to driver leads 156, 158 are wired to correspond to signal lines 1802, 1804 shown in FIG. 18, respectively, and signal line 1805 is disconnected. The first amplifier 1810 would sense a voltage of alternating polarity corresponding to red LED and infrared LED drive signals, and the second amplifier 1820 and third amplifier 1830 would sense nothing. Hence, an alternating output voltage from only the first amplifier 1810 would indicate to the switch control 1712 in FIG. 17 that the driver 1704 is configured for back-to-back LEDs.

As illustrated in FIG. 18, by contrast, if the monitor driver is configured for common-anode LEDs, then, as illustrated in FIG. 6, the equivalent to driver leads 352, 354, 355 are wired to correspond to signal lines 1802, 1804, 1805, shown in FIG. 18, respectively. The first amplifier 1810 would sense a unipolar voltage corresponding to the red LED drive signal. The second amplifier 1820 would sense a unipolar voltage corresponding to the infrared LED drive signal. The third amplifier 1830 would sense nothing. Hence, alternating output voltages from the first amplifier 1810 and the second amplifier 1820 would indicate to the switch control 1712 in FIG. 17 that the driver 1704 is configured for common-cathode LEDs. By comparison, if the monitor driver is configured for common cathode LEDs, a different two of the amplifiers 1810, 1820, 1830 would sense similar voltages as in the common-anode case. Thus, the outputs of the amplifiers 1810, 1820, 1830 provide sufficient information to the first switch control 1712 in FIG. 17 to determine the driver configuration.

As illustrated in FIG. 17, it is assumed that a sensor 1502 has three possible LED configurations 1702. That is, an attached sensor will have either back-to-back LEDs, common-anode LEDs or common-cathode LEDs. Thus, the configuration adapter 1700 has three signal lines 1582 from the sensor LEDs 1702. For example, as illustrated in FIG. 6, a back-to-back LED sensor 412 has two leads 106, 108 that correspond to two of the three signal lines 1582, leaving one of the three signal lines 1582 unused. As illustrated in FIG. 7 as another example, a common-anode sensor 412 has three leads 302, 304, 305 that correspond to the three signal lines 1582.

FIG. 18 illustrates an embodiment of the LED test 1720. The LED test 1720 looks at the three signal lines 1582 to determine the sensor configuration. The LED test circuit 1720 shown has a voltage source 1850 and two differential amplifiers 1860, 1870 that provide a return path for the voltage source 1850. To test the sensor LED configuration, a switch 1880 alternately connects the voltage source 1850 to each of the three signal lines 1582 and, at the same time, connects the differential amplifiers 1860, 1870 to the remaining two signal lines 1582. For example, in a first position 1882 (depicted), the output of the voltage source 1850 is connected to a first signal line 1806, the input of the first amplifier 1860 is connected to a second signal line 1808, and the input of the second amplifier 1870 is connected to a third signal line 1809.

If a sensor has back-to-back LEDs, then, as illustrated in FIG. 6, the equivalent to sensor leads 106, 108 are wired to correspond to signal lines 1806, 1808 shown in FIG. 18, respectively, and signal line 1809 is disconnected. In the first switch position 1882, the voltage source 1850 drives the red LED and current is detected by the first amplifier 1860. In the second position 1884, the voltage source 1850 drives the infrared LED and current is detected by the first amplifier 1860. In the third switch position 1886, the voltage source 1850 drives the disconnected line 1809 and no current is detected by either amplifier 1860, 1870. Hence, a voltage output from the first amplifier 1860 at the first and second switch positions 1882, 1884, with no amplifier output at the third switch position 1886, indicates that the sensor has back-to-back LEDs.

As illustrated in FIG. 18, by contrast, if the sensor is configured for common-anode LEDs, then, as illustrated in FIG. 7, the equivalent to driver leads 302, 304, 305 are wired to correspond to signal lines 1806, 1808, 1809, shown in FIG. 18, respectively. In the first switch position 1882, the voltage source 1850 drives the anodes of both LEDs, but a current path is only provided by the input to the first amplifier 1860, which produces a corresponding output. In the second and third switch positions 1884, 1886 the voltage source 1850 back biases both LEDs and no current is detected by either amplifier 1860, 1870. Hence, a voltage output from the first amplifier 1860 at the first switch position 1882, with no amplifier outputs at the second and third switch positions 1884, 1886, indicates that the sensor has common-anode LEDs. By comparison, if the sensor has common-cathode LEDs, in the first switch position 1882, the voltage source 1850 would back-bias the diodes and no current would be detected by either amplifier 1860, 1870. In the second and third positions 1884, 1886, current would be detected by the first and second amplifiers 1860, 1870, respectively. Thus, the outputs of the amplifiers 1860, 1870 provide sufficient information to the second switch control 1722 in FIG. 17 to determine the sensor LED configuration.

As illustrated in FIG. 17, the switch control 1712 could be a simple state machine. After the LED test 1720 cycles through the three positions of the switch 1880 shown in FIG. 18, and after the driver test 1710 senses driver activation, the switch control 1712 would latch the first and second bi-direction switches 1530, 1580 to connect the appropriate adapter element to the signal lines 1532, 1582. For example, if back-to-back LEDs 1702 were detected and a common-anode driver 1704 was detected, the bi-directional switches 1530, 1580 would connect the three signal lines 1532, 1582 to the common-anode (CA) to back-to-back (BB) adapter element 1734. The CA to BB adapter element is described above with respect to FIG. 6.

As illustrated in FIG. 15, a simplified embodiment of the universal adapter 1500 is possible if the sensor 1502 is of a known configuration. For example, a sensor manufacturer may wish to provide a universal adapter 1500 between their particular sensors and most or all pulse oximetry monitors. In that case, there would be fewer combinations of adapter elements 1540 and the first switch 1530 and second switch 1580 would be simpler accordingly. For example, as illustrated in FIG. 17, if it is known that the sensor 1502 has back-to-back LEDs 1702, then only the "straight-through" 1731, "CA to BB" 1734 and "CC to BB" 1736 adapter elements are required. Correspondingly, the first switch 1530 and second switch 1580 would be equivalent to bidirectional one-line to three-line multiplexers, rather than the more complex one-line to seven-line multiplexers shown.

One would appreciate that testing and switching circuitry, such as shown in FIG. 17, is also applicable to embodiments of, for example, drive limit portions and information translator portions of the universal adapter 1500 shown in FIG. 15. Further, one will recognized that portions of the sensor adapter shown in FIGS. 4 and 15 could be implemented with microcontroller or microprocessor circuitry and associated firmware rather than in hardwired circuitry. Also, particular adapter elements might be selected manually, such as with hand-actuated switches, rather than through automatic sensing of the sensor and monitor configurations as described above. As another alternative to automatic sensing of the sensor and monitor configurations, particular connector adapters 1560, 1510 could contain coding elements that function as indicators of the corresponding sensor 1502 or monitor 1504 configurations.

The pulse oximetry sensor adapter has been disclosed in detail in connection with the preferred embodiments of the present invention. These embodiments are disclosed by way of examples only and are not to limit the scope of the present invention, which is defined by the claims that follow. One in the art will appreciate many variations and modifications within the scope of this invention.

What is claimed is:

1. An adapter configured to connect one noninvasive optical sensor from a variety of possible noninvasive optical sensors to one patient monitor from a variety of possible patient monitors to create a pulse oximetry system, the adapter comprising:
   a first connector adapter attachable to a monitor;
   a second connector adapter attachable to a sensor; and
   a sensor adapter cable coupled between the first connector adapter and the second connector adapter, wherein the sensor adapter cable comprises:
      a monitor selector that senses a drive configuration or drive levels of the monitor;
      a sensor selector that determines a light emitting diode configuration;
      a plurality of adapter elements that modify signals between the monitor and the sensor for compatible operations;
      a first switching circuit that couples a selected adapter element to the first connector adapter based on outputs from the monitor selector and the sensor selector, wherein the selected adapter element is one of the plurality of adapter elements; and
      a second switching circuit that couples the selected adapter element to the second connector adapter.

2. The adapter of claim 1 wherein the sensor adapter cable has generic connectors at each end with predetermined signal pinouts, the first connector adapter is a cross-wired cable with a generic connector at one end for mating with the first generic connector of the sensor adapter cable and a specific connector at another end for mating with a specific type of monitor, and the second connector adaptor is a cross-wired cable with a generic connector at one end for mating with the second generic connector of the sensor adapter cable and a specific connector at another end for mating with a specific type of sensor.

3. The adapter of claim 2 wherein the monitor selector tests signal lines from the first generic connector of the sensor adapter cable to determine the drive configuration or the drive levels of the monitor while the sensor selector tests signal lines from the second generic connector of the sensor adapter cable to determine the light emitting diode configuration or presence of the information element in the sensor.

4. The adapter of claim 1 wherein the first switching circuit and the second switching circuit are bi-directional multiplexers.

5. The adapter of claim 1 wherein one of the plurality of adapter elements is a straight-through adapter for coupling a monitor with a normally compatible sensor.

6. The adapter of claim 1 wherein the monitor selector determines the drive configuration based on three signal lines connectable to the monitor, and the monitor selector comprises three differential amplifiers with each of the differential amplifiers having inputs coupled across a unique pair of the three signal lines.

7. The adapter of claim 1 wherein the sensor selector determines the light emitting diode configuration based on three signal lines connectable to the sensor, and the sensor selector comprises a voltage source that selectively connects to one of the three signal lines while two amplifiers selectively connect to the remaining two of the three signal lines.

8. A method to connect one sensor from a variety of possible sensors to one monitor from a variety of possible monitors to form an operable pulse oximetry system capable of monitoring blood parameters of a patient, the method comprising:
attaching a patient monitor to a first end of an adapter cable;
attaching a sensor to a second end of the adapter cable;
sensing a driver configuration of the monitor based on a first set of signal lines at the first end of the adapter cable;
sensing a light emitting diode configuration of the sensor based on a second set of signal lines at the second end of the adapter cable;
selecting an adapter element from a plurality of adapter elements in the adapter cable to provide drive signals from said monitor to properly drive light source elements of said sensor and to provide detector signals from said sensor to properly be received by signal conditioning elements of said monitor to form an operable pulse oximetry system from said monitor, said adapter cable, and said sensor.

9. The method of claim 8 wherein attaching the monitor to the first end of the adapter cable comprises:
using an attachment cable with a specific connector at one end and a generic connector at another end, wherein the specific connector mates with a monitor connector and the generic connector mates with an adapter connector at the first end of the adapter cable; and
cross-wiring one or more cable wires between the specific connector and the generic connector in the attachment cable to match predetermined pinouts in the adapter connector.

10. The method of claim 8 wherein attaching the sensor to the second end of the adapter cable comprises:
using an attachment cable with a specific connector at one end and a generic connector at another end, wherein the specific connector mates with a sensor connector and the generic connector mates with an adapter connector at the second end of the adapter cable; and
cross-wiring one or more cable wires between the specific connector and the generic connector in the attachment cable to match predetermined pinouts in the adapter connector.

11. The method claim 8 wherein sensing the driver configuration of the monitor comprises detecting a differential voltage across at least one pair of signal lines in the first set of signal lines.

12. The method of claim 8 wherein sensing the light emitting diode configuration of the sensor comprises driving the signal lines in the second set of signal lines one at a time while detecting for current in the remaining signal lines.

13. The method of claim 8 wherein the first set of signal lines and the second set of signal lines comprise three signal lines each.

14. The method of claim 8 wherein bi-directional switches couple the selected adapter element to the appropriate signal lines.

15. A method of providing appropriate communication between a blood parameter monitor and a noninvasive sensor, the method comprising:
attaching a monitor to a first standard connector at a first end of a sensor adapter cable;
attaching a sensor to a second standard connector at a second end of the sensor adapter cable;
testing a first set of signal lines in the first standard connector to determine monitor type;
testing a second set of signal lines in the second standard connector to determine sensor type; and
based on said testing of the first and second set of signal lines, electrically connecting adapter elements to provide appropriate communication from said monitor to said sensor to drive light source elements and to provide appropriate communication from said sensor to said monitor to convey detector element signals to circuit conditioning elements of said monitor in a manner usable to determine one or more blood parameters from said detector element signals.

* * * * *

UNITED STATES PATENT AND TRADEMARK OFFICE
CERTIFICATE OF CORRECTION

PATENT NO.       : 7,844,313 B2
APPLICATION NO.  : 11/341999
DATED            : November 30, 2010
INVENTOR(S)      : Massi E. Kiani et al.

It is certified that error appears in the above-identified patent and that said Letters Patent is hereby corrected as shown below:

At column 18, line 7, delete "bidirectional" and insert therefore, --bi-directional--.

At column 20, line 18, delete "method claim" and insert therefore, --method of claim--.

Signed and Sealed this
Sixth Day of December, 2011

David J. Kappos
*Director of the United States Patent and Trademark Office*